US006786054B2

(12) United States Patent
Voute et al.

(10) Patent No.: US 6,786,054 B2
(45) Date of Patent: Sep. 7, 2004

(54) SYSTEMS AND METHODS FOR FREEZING, STORING AND THAWING BIOPHARMACEUTICAL MATERIAL

(75) Inventors: Nicholas Voute, Cuges les Pins (FR); Maxime N. Lok, Marseille (FR); David C. Brown, Chicago, IL (US); James W. Kendall, Mount Prospect, IL (US); Edward Geiselhart, Chicago, IL (US)

(73) Assignee: Integrated Biosystems, Inc., Napa, CA (US)

( * ) Notice: Subject to any disclaimer, the term of this patent is extended or adjusted under 35 U.S.C. 154(b) by 0 days.

(21) Appl. No.: 10/744,967

(22) Filed: Dec. 22, 2003

(65) Prior Publication Data

US 2004/0134203 A1 Jul. 15, 2004

Related U.S. Application Data

(63) Continuation of application No. 10/254,025, filed on Sep. 23, 2002, now Pat. No. 6,684,646, which is a continuation-in-part of application No. 09/905,488, filed on Jul. 13, 2001, now Pat. No. 6,453,683, which is a continuation-in-part of application No. 09/863,126, filed on May 22, 2001, now Pat. No. 6,635,414.
(60) Provisional application No. 60/334,622, filed on Nov. 1, 2001.

(51) Int. Cl.[7] .................................................. F25C 1/00
(52) U.S. Cl. ............................. 62/66; 62/356; 249/127
(58) Field of Search ........................ 62/66, 340, 356; 248/95; 249/112, 121, 127, 130

(56) References Cited

U.S. PATENT DOCUMENTS

| 2,662,520 A | 12/1953 | McMahon ..................... 128/1 |
| 2,775,101 A | 12/1956 | Hanson ......................... 62/108 |
| 2,964,920 A | * 12/1960 | Staebler ......................... 62/60 |
| 2,966,041 A | * 12/1960 | Zearfoss, Jr. et al. ........... 62/60 |
| 3,121,627 A | 2/1964 | Harris ............................ 62/58 |
| 3,389,974 A | 6/1968 | Barattini et al. .............. 23/295 |
| 3,940,232 A | * 2/1976 | Stock .......................... 425/447 |
| 3,959,981 A | 6/1976 | Anderson .................... 62/135 |
| 4,030,314 A | 6/1977 | Strehler et al. ................ 62/65 |
| 4,090,374 A | 5/1978 | Faust et al. .................. 62/341 |
| 4,107,937 A | 8/1978 | Chimiel ........................ 62/64 |
| 4,178,776 A | 12/1979 | Baldus et al. ................ 62/538 |

(List continued on next page.)

FOREIGN PATENT DOCUMENTS

| DE | 3047784 A1 | 7/1982 | ............ C12N/5/00 |
| DE | 3833753 A1 | 8/1989 | ............ F25D/3/10 |
| DE | 4029216 | 3/1992 | |

(List continued on next page.)

OTHER PUBLICATIONS

Stahl, A.L., "Concentration of Citrus Juices by Freezing", Florida State Horticultural Society, 1944, pp. 43–45.
Kalhori, B. et al., "Studies on Heat Transfer From a Vertical Cylinder, With or Without Fins, Embedded in a Solid Phse Change Mediam", Transactions of the ASME, Journal of Heat Transfer, vol. 107, Feb. 1985, pp. 44–51.

(List continued on next page.)

Primary Examiner—William E. Tapolcai
(74) Attorney, Agent, or Firm—Heslin Rothenberg Farley & Mesiti P.C.; Nicholas Mesiti, Esq.; Victor A. Cardona, Esq.

(57) ABSTRACT

A system for controlled freezing, storing and thawing a biopharmaceutical material includes a flexible container and a supporting structure. The flexible container is adapted to receive the biopharmaceutical material therein for freezing, storing and thawing. The container further includes a flange and the supporting structure is engageable with the flange to receive the container. The supporting structure may position the container for freezing and may protect it during transport and storage.

36 Claims, 30 Drawing Sheets

U.S. PATENT DOCUMENTS

| | | | |
|---|---|---|---|
| 4,304,293 A | 12/1981 | Scheiwe et al. | 165/12 |
| 4,327,799 A | 5/1982 | Scheiwe et al. | 165/2 |
| 4,336,435 A | 6/1982 | Kashyap et al. | 219/10.55 |
| 4,473,739 A | 9/1984 | Scheiwe et al. | 219/302 |
| 4,486,389 A | 12/1984 | Darnell et al. | 422/307 |
| 4,490,982 A | 1/1985 | Christmas | 62/3 |
| 4,531,373 A | 7/1985 | Rubinsky | 62/63 |
| 4,580,409 A | 4/1986 | Angelier et al. | 62/340 |
| 4,584,843 A | 4/1986 | Pronger, Jr. et al. | 62/123 |
| 4,587,810 A * | 5/1986 | Fletcher | 62/3.63 |
| 4,596,120 A | 6/1986 | Knodel et al. | 62/59 |
| 4,609,036 A | 9/1986 | Schrader | 165/10 |
| 4,669,271 A | 6/1987 | Noel | 62/60 |
| 4,712,607 A | 12/1987 | Lindeman et al. | 165/30 |
| 4,793,151 A | 12/1988 | Masel et al. | 62/306 |
| 4,799,358 A | 1/1989 | Knopf et al. | 62/3 |
| 4,801,777 A | 1/1989 | Auerbach | 219/10.55 |
| 4,843,827 A | 7/1989 | Peppers | 62/73 |
| 4,874,915 A | 10/1989 | Harms et al. | 219/10.55 |
| 4,893,670 A | 1/1990 | Joshi et al. | 165/40 |
| 4,954,679 A | 9/1990 | Harms et al. | 219/10.55 |
| 4,967,564 A | 11/1990 | Strasser | 62/47.1 |
| 4,971,737 A * | 11/1990 | Infanti | 264/28 |
| 4,976,308 A | 12/1990 | Faghri | 165/10 |
| 4,986,080 A | 1/1991 | Grigoli et al. | 62/75 |
| 5,005,371 A | 4/1991 | Yonezawa et al. | 62/238.6 |
| 5,022,149 A | 6/1991 | Abbott | 29/890.048 |
| 5,029,634 A | 7/1991 | Hurner | 165/47 |
| 5,033,544 A | 7/1991 | Abbott | 165/184 |
| 5,054,548 A | 10/1991 | Zohler | 165/133 |
| 5,072,569 A | 12/1991 | VanTassel | 52/745 |
| 5,090,207 A | 2/1992 | Gilbertson et al. | 62/59 |
| 5,125,900 A | 6/1992 | Teves | 604/114 |
| 5,168,725 A | 12/1992 | Margolin | 62/457.9 |
| 5,176,197 A | 1/1993 | Hamaguchi et al. | 164/459 |
| 5,181,387 A | 1/1993 | Meckler | 62/59 |
| 5,212,957 A | 5/1993 | Ruff | 62/124 |
| 5,220,954 A | 6/1993 | Longardner et al. | 165/10 |
| 5,243,833 A | 9/1993 | Coelho et al. | 62/376 |
| 5,285,657 A | 2/1994 | Bacchi et al. | 62/457.9 |
| 5,332,034 A | 7/1994 | Chiang et al. | 165/184 |
| 5,374,436 A | 12/1994 | White et al. | 426/249 |
| 5,411,078 A | 5/1995 | Ares | 165/113 |
| 5,458,191 A | 10/1995 | Chiang et al. | 165/133 |
| 5,476,763 A | 12/1995 | Bacchi et al. | 435/284.1 |
| 5,520,885 A | 5/1996 | Coelho et al. | 422/101 |
| 5,524,706 A | 6/1996 | Nakamura et al. | 165/47 |
| 5,535,598 A | 7/1996 | Cothern et al. | 62/356 |
| 5,557,943 A | 9/1996 | Coelho et al. | 62/376 |
| 5,579,830 A | 12/1996 | Giammaruti | 165/104.27 |
| 5,582,856 A | 12/1996 | White et al. | 426/249 |
| 5,609,035 A | 3/1997 | Cothern et al. | 62/73 |
| 5,616,268 A | 4/1997 | Carr | 219/687 |
| 5,638,686 A | 6/1997 | Coelho et al. | 62/51.1 |
| 5,644,922 A | 7/1997 | Linden et al. | 62/51.1 |
| 5,689,961 A | 11/1997 | Cosman | 62/78 |
| 5,750,658 A | 5/1998 | Coelho et al. | 530/382 |
| 5,779,974 A | 7/1998 | Kuzyk | 422/44 |
| 5,862,675 A | 1/1999 | Scaringe et al. | 62/193.3 |
| 5,863,715 A | 1/1999 | Rajotte et al. | 435/1.3 |
| 5,873,254 A | 2/1999 | Arav | 62/63 |
| 5,884,490 A | 3/1999 | Whidden | 62/70 |
| 5,939,023 A | 8/1999 | Coelho et al. | 422/101 |
| 5,964,095 A | 10/1999 | Coelho et al. | 62/62 |
| 5,964,100 A | 10/1999 | Wisniewski | 62/373 |
| 5,988,422 A | 11/1999 | Vallot | 220/62.22 |
| 5,999,701 A | 12/1999 | Schmidt | 392/470 |
| 6,007,773 A | 12/1999 | Kuzyk | 422/44 |
| 6,065,294 A | 5/2000 | Hammerstedt et al. | 62/3.3 |
| 6,077,447 A | 6/2000 | Coelho et al. | 210/774 |
| 6,079,215 A | 6/2000 | Wisniewski | 62/46.1 |
| 6,098,410 A | 8/2000 | Horigane | 62/62 |
| 6,123,696 A | 9/2000 | Coelho et al. | 604/410 |
| 6,146,124 A | 11/2000 | Coelho et al. | 425/387.1 |
| 6,196,296 B1 | 3/2001 | Wisniewski et al. | 165/47 |
| 6,220,038 B1 | 4/2001 | Marsh et al. | 62/71 |
| 6,232,115 B1 | 5/2001 | Coelho et al. | 435/307.1 |
| 6,274,090 B1 | 8/2001 | Coelho et al. | 422/101 |
| 6,302,327 B1 | 10/2001 | Coelho et al. | 235/383 |
| 6,371,121 B1 | 4/2002 | Faries, Jr. et al. | 128/849 |
| 6,384,380 B1 | 5/2002 | Faries, Jr. et al. | 219/385 |
| 6,387,322 B1 | 5/2002 | Gallus | 422/38 |
| 6,453,683 B1 | 9/2002 | Wisniewski et al. | 62/75 |

FOREIGN PATENT DOCUMENTS

| | | | |
|---|---|---|---|
| EP | 0195919 A2 | 2/1986 | A23B/4/06 |
| EP | 0318924 | 6/1989 | |
| EP | 0647707 A2 | 7/1994 | C12M/1/00 |
| EP | 0726080 A2 | 12/1995 | |
| FR | 758510 | 1/1934 | |
| GB | 2196830 A | 5/1988 | |
| GB | 2240165 A | 7/1991 | |
| GB | 2351799 A | 1/2001 | |
| WO | WO 97/24152 | 7/1997 | A61M/1/36 |
| WO | WO/9823907 | 6/1998 | |
| WO | WO 98/34078 | 8/1998 | |

OTHER PUBLICATIONS

Wisniewski, et al., "Large–Scale Freezing and Thawing of Biopharmaceutical Drug Product", Proceedings of the International Congress: Advanced Technologies For Manufacturing Of Aseptic & Terminally Sterilized Pharmaceuticals & Biopharmaceuticals, Basel, Switzerland, Feb. 17–19, 1992, pp. 132–140.

Wisniewski, et al., "Large–Scale Freezing and Thawing of Biopharmaceutical Products", Biotechnology and Biopharmaceutical Manufacturing, Processing and Preservation, pp. 7–59.

Wisniewski, Richard, "Developing Large–Scale Cryopreservation Systems for Biopharmaceutical Products", BioPharm, Jun. 1998, pp. 50–60.

Wu, et al., "Scale–Down Approach to Large Volume Cryopreservation of Biopharmaceuticals Using the CryoCassette™ and Cryowedge™", Integrated Biosystems, 2000, 4 pages.

L. Quan et al., "Effects of Vibration on Ice Contact Melting Within Rectangular Enclosures", Transactions of the ASME 120:518–520 (May 1998).

Burton et al., "An Experimental Investigation of the Solidification Process in a V–Shaped Sump", Inter. J. Heat Mass Transfer, vol. 18, pp. 2383–2393, 1995.

Avis et al., *Cryopreservation Applications in Pharmaceuticals and Biotechnology*, Drug Manufacturing Technology Series 5, "Large–Scale Cryopreservation: Process Development for Freezing and Thawing of Large Volumes of Cell Suspensions, Protein Solutions, and Biological Products", Wisniewski, pp. 181–197.

* cited by examiner

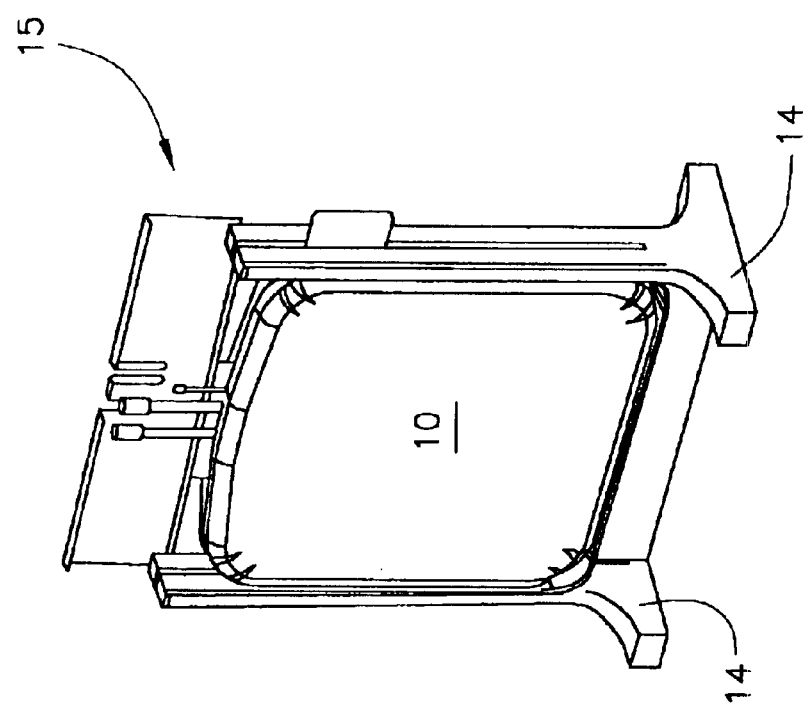
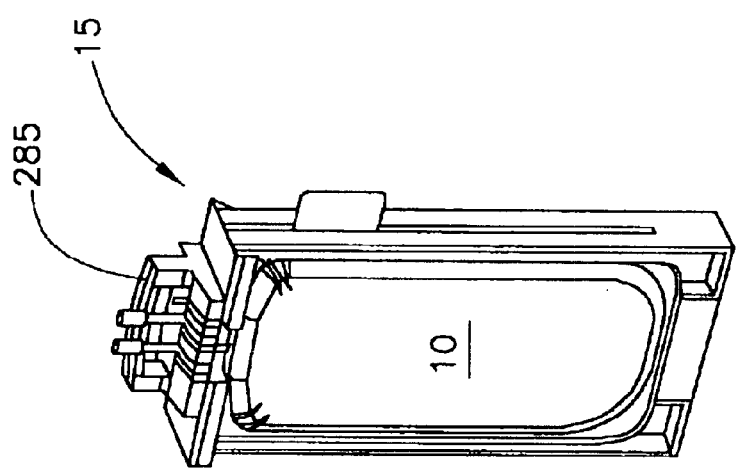
FIG. 4
FIG. 3

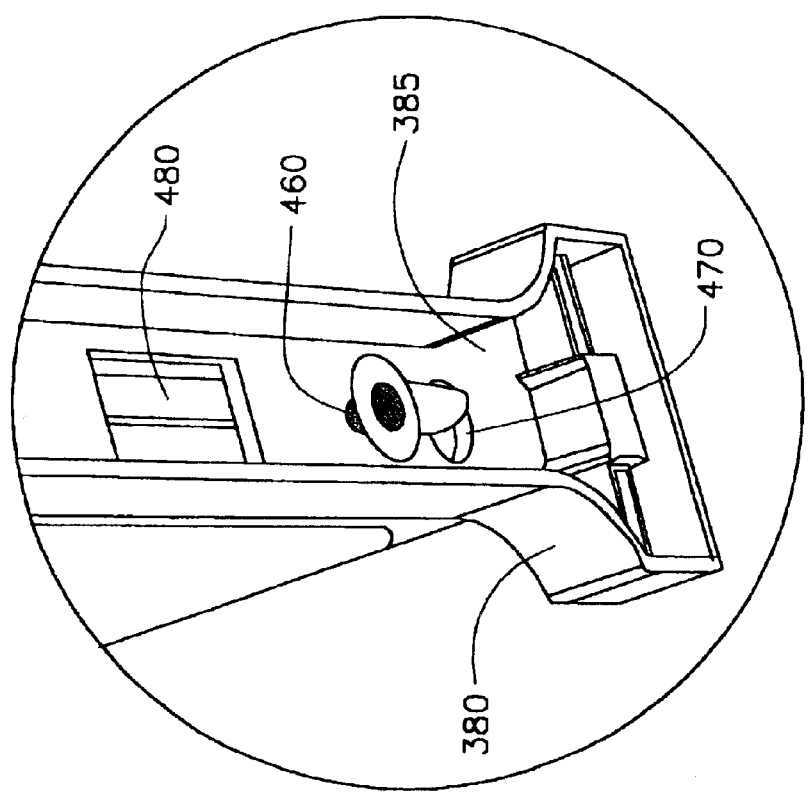

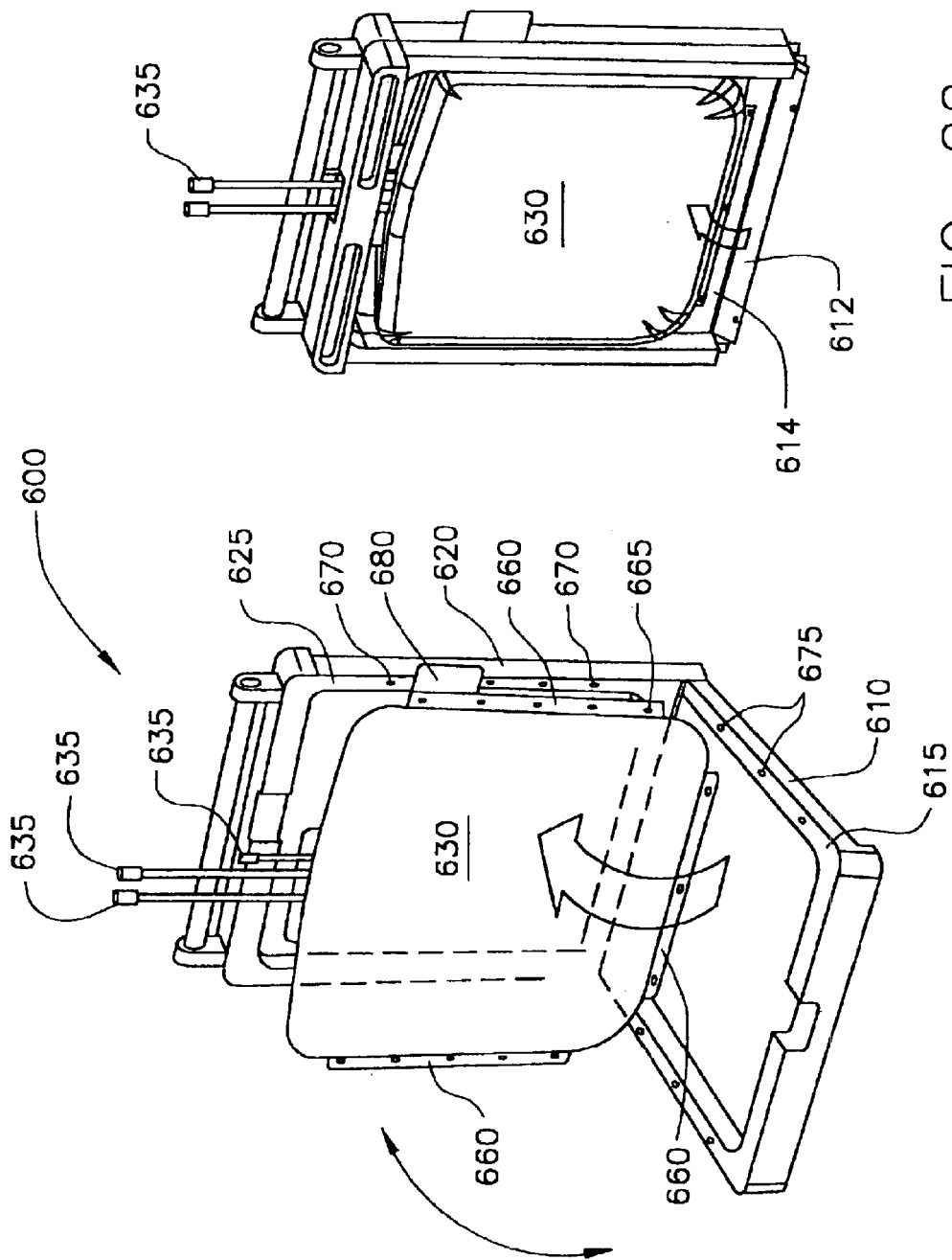

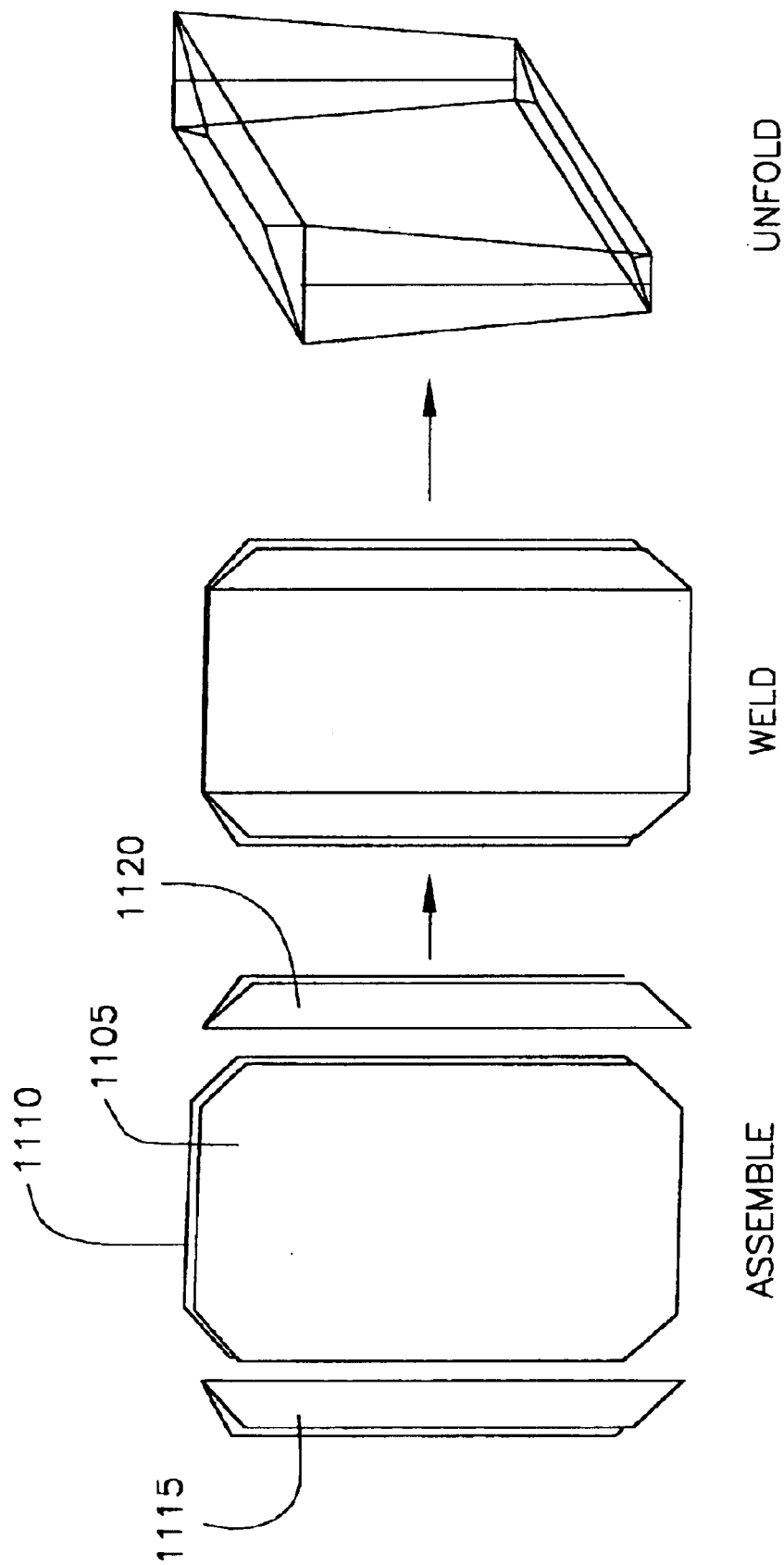

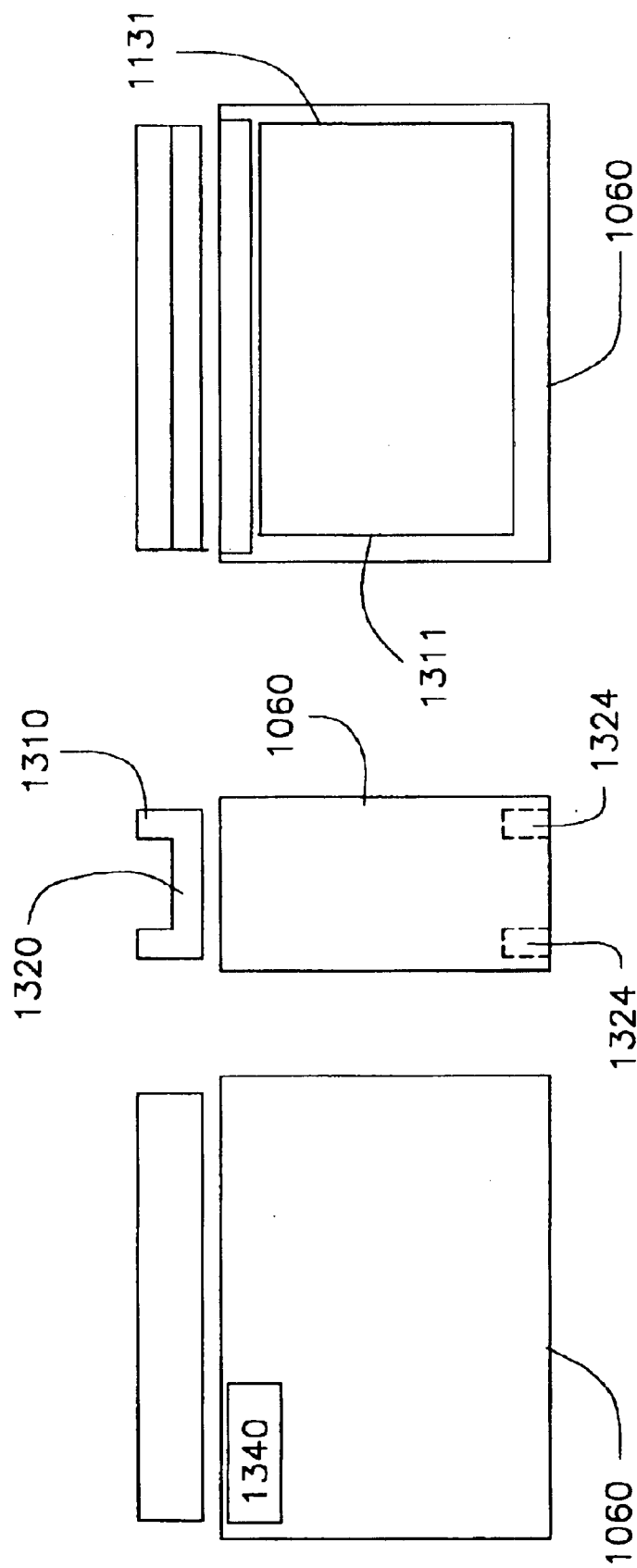

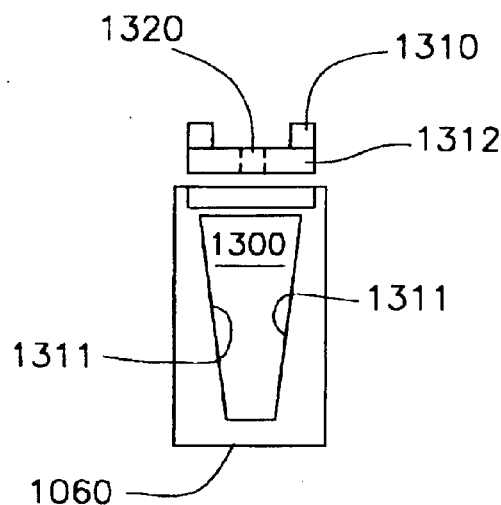
FIG. 41
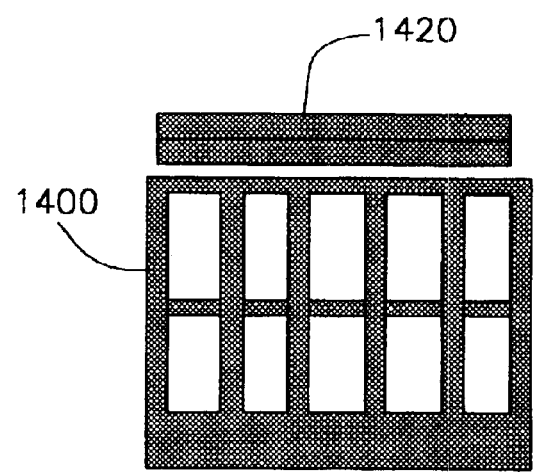
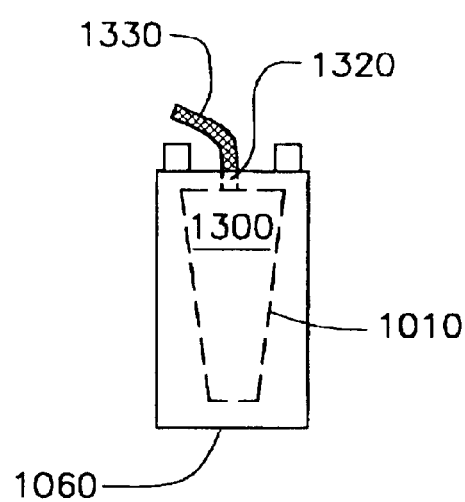
FIG. 42
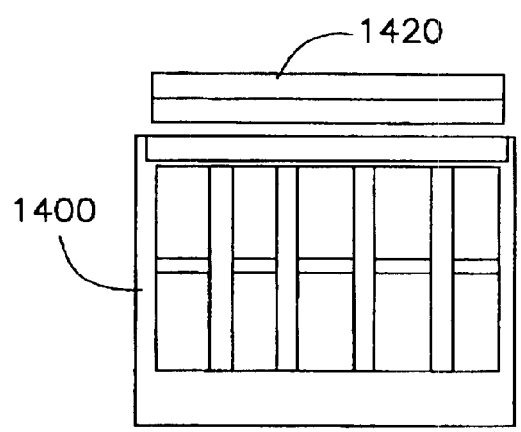
FIG. 43

SYSTEMS AND METHODS FOR FREEZING, STORING AND THAWING BIOPHARMACEUTICAL MATERIAL

CROSS-REFERENCE TO RELATED APPLICATIONS

This application is a Continuation of U.S. Ser. No. 10/254, 025, filed Sep. 23, 2002 now U.S. Pat. No. 6,684,646, which claims the benefit of U.S. Provisional application No. 60/334,622, filed Nov. 1, 2001, the disclosure of which is incorporated by reference. U.S. Ser. No. 10/254,025, is also a Continuation-In-Part of U.S. patent application Ser. No. 09/905,488, filed Jul. 13, 2001, now U.S. Pat. No. U.S. 6,453,683, issued Sep. 24, 2002, entitled Cryopreservation System with Controlled Dendritic Freezing Front Velocity, which is a continuation-in-part of U.S. patent application Ser. No. 09/863,126 filed May 22, 2001, now U.S. Pat. No. 6,635,414, issued Oct. 21, 2003, the disclosures all of which are incorporated by reference. Further, this application relates to U.S. patent application Ser. No. 10/254,036, filed Sep. 23, 2002, and U.S. patent application Ser. No. 10/724, 793, filed Dec. 1, 2003, both entitled Systems and Methods for Freezing and Storing Biopharmaceutical Material, the entireties of which are incorporated herein by reference.

TECHNICAL FIELD

This invention relates, in general, to biopharmaceutical materials, preservation methods and systems, and more particularly to systems and methods for transporting, freezing, storing, and thawing of biopharmaceutical materials.

BACKGROUND ART

Preservation of biopharmaceutical materials is important in the manufacture, storage, sale and use of such materials. For example, biopharmaceutical materials are often preserved by freezing between processing steps and during storage. Similarly, biopharmaceutical materials are often frozen during transportation between manufacturing locations.

Currently, preservation of biopharmaceutical material often involves placing a container containing liquid biopharmaceutical material in a cabinet freezer, chest freezer or walk-in freezer and allowing the biopharmaceutical material to freeze. Specifically, the container is often placed on a shelf in the cabinet freezer, chest freezer or walk-in freezer and the biopharmaceutical material is allowed to freeze. These containers may be stainless-steel vessels, plastic bottles or carboys, or plastic bags. They are typically filled with a specified volume to allow for freezing and expansion and then transferred into the freezers at temperatures typically ranging from negative 20 degrees Celsius to negative 70 degrees Celsius or below.

To ensure efficient use of available space inside the freezer, containers are placed alongside one another and sometimes are stacked into an array with varied spatial regularity. Under these conditions, cooling of the biopharmaceutical solution occurs at different rates depending on the exposure of each container to the surrounding cold air, and the extent to which that container is shielded by neighboring containers. For example, containers placed close to the cooling source or those on the outside of an array of containers would be cooled more rapidly than those further away from the cooling source and/or situated at the interior of the array.

In general, adjacent placement of multiple containers in a freezer creates thermal gradients from container to container. The freezing rate and product quality then depend on the actual freezer load, space between the containers, and air movement in the freezer. This results in a different thermal history for the contents of the containers depending on their location in a freezer, for example. Also, the use of different containers for individual portions of a single batch of biopharmaceutical material may cause different results for portions of the same batch due to different thermal histories resulting from freezing in a multiple container freezer, particularly if the storage arrangement is haphazard and random. Another consequence of obtaining a range of freezing times is that certain containers may freeze so slowly that the target solute can no longer be captured within the ice phase, but remains in a progressively smaller liquid phase. This phenomenon is referred to as "cyroconcentration." In some cases such cyroconcentration could result in precipitation of the biopharmaceutical product, thus resulting in product loss.

Disposable containers such as plastic bags or other flexible containers often are damaged, leading to loss of the biopharmaceutical material. Particularly, the volumetric expansion of the biopharmaceutical materials during freezing could generate excessive pressure in an over filled bag or in a pocket of occluded liquid adjoining the bag material, possibly leading to rupture or damage to the integrity of the bag. Moreover, handling of such disposable containers, such as plastic bags, during freezing, thawing, or transportation of these containers often result in damage thereof, due, for example, to shock, abrasion, impact, or other mishandling events arising from operator errors or inadequate protection of the bags in use.

Thus, there is a need for systems and methods for freezing, storing, and thawing of biopharmaceutical materials that are controlled, do not result in loss of biopharmaceutical material, but instead create conditions conducive to preserving the biopharmaceutical material in a uniform, repeatable fashion in a protected environment.

SUMMARY OF THE INVENTION

The present invention provides, in a first aspect, a container for freezing, storing and thawing a biopharmaceutical material, which is receivable in a frame for supporting and protecting said container. The container includes a material adapted to receive the biopharmaceutical material therein for freezing, storing and thawing in liquid or frozen state, and the container includes a flange connectable to the support frame for supporting the flexible container in the support frame.

The present invention provides, in a second aspect, a system for freezing, storing and thawing a biopharmaceutical material which includes a container and a frame. The container is adapted to receive the biopharmaceutical material therein and the container includes a flange. The frame is adapted to receive the container and is engagable with the flange.

The present invention provides, in a third aspect, a method for freezing, storing and thawing a biopharmaceutical material. The method includes providing a container adapted to contain the biopharmaceutical material for freezing, storing and thawing, and positioning the container in a frame for supporting and protecting the container.

The present invention provides, in a fourth aspect, a system for freezing, storing and thawing a biopharmaceutical material which includes a container adapted to receive the biopharmaceutical material therein for freezing, storing and thawing. The container is adapted to receive a support member for supporting the container.

The present invention provides, in a fifth aspect, a method for freezing, storing and thawing a biopharmaceutical material. The method includes providing a container adapted to contain the biopharmaceutical material for freezing, storing and thawing and connecting a sleeve of the container to a support member.

The present invention provides, in a sixth aspect, a system for freezing, storing and thawing a biopharmaceutical material which includes a container adapted to receive biopharmaceutical material therein for freezing and subsequent thawing. The container is configured to conform to the shape of an interior of a temperature control unit, when the container is substantially filled with the biopharmaceutical material, and/or the shape of a protective structure adapted to receive the container.

The present invention provides, in a seventh aspect, a system for freezing, storing and thawing a biopharmaceutical material which includes a flexible container adapted to contain the biopharmaceutical material. The flexible container is adapted to substantially conform to a shape of a first interior of a temperature control unit and is adapted to substantially conform to a second interior of a storage vessel.

The present invention provides, in a eighth aspect, a method for freezing, storing and thawing a biopharmaceutical material which includes providing a sterile container adapted to contain the biopharmaceutical material for freezing and configuring the sterile container to conform to a shape of an interior of a temperature control unit.

The present invention provides, in a ninth aspect, a system for storing a biopharmaceutical material which includes a flexible container configured to contain the biopharmaceutical material for freezing wherein the flexible container further includes means for engaging with at least one of a temperature control unit and a storage vessel for supporting the flexible container.

The present invention provides, in a tenth aspect, a system for freezing, storing and thawing biopharmaceutical material which includes a flexible container, a conduit, and a temperature control unit. The flexible container is adapted to receive a liquid biopharmaceutical material therein for freezing, storing and thawing, wherein the container fully encloses an interior portion for receiving the biopharmaceutical material. Also, the container is configured to form a three-dimensional shape when filled with the biopharmaceutical material wherein the three dimensional shape has a first side and a second side opposite the first side. The conduit is connected to the flexible container to allow the outside of the container to be in fluid communication with the interior portion via the conduit. The temperature control unit includes a first surface and a second surface facing the first surface. Also, the temperature control unit is configured to receive the flexible container therein, when the container is filled with the biopharmaceutical material. The container conforms to the shape of the interior of the temperature control unit and the first side and the second side of the container contact the first surface and the second surface of the temperature control unit, when the container is substantially filled with the biopharmaceutical material. The first and/or second surfaces of the temperature control unit include a heat transfer surface.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

FIG. 3 is a perspective view of another example of a flexible container of smaller capacity than that depicted in FIG. 2 being received in a frame, in accordance with the present invention;

FIG. 4 is a perspective view of another example of a frame holding the flexible container of FIG. 2, wherein the frame includes foot members;

FIG. 14 is a perspective view of the cart of FIG. 13 adjacent the temperature control unit of FIG. 5 for transporting the frame of FIG. 2 there between;

FIG. 19 is a perspective view of a portion of the frame of FIG. 15 illustrating a tie-down loop of the flexible container being connected to a tie-down boss of the frame;

FIG. 21 is a perspective view of the flexible container and frame of FIG. 20 in an open position depicting the flexible container being positioned in the frame;

FIG. 22 is a perspective view of the flexible container and frame of FIG. 20 depicting a pivoting side being closed;

FIG. 34 is a perspective view of portions of a container for storing and freezing biopharmaceutical materials in the form of a flexible container useable in the system of FIG. 33 prior to assembly thereof.;

FIG. 35 is a perspective view of pieces of the flexible container of FIG. 34 after they have been welded;

FIG. 36 is a perspective view of the flexible container of FIG. 35 after it has been assembled;

FIG. 38 is a side elevational view of a storage structure useable in the system depicted in FIG. 33 for receiving a flexible container for holding biopharmaceutical material;

FIG. 39 is an end elevational view of the storage structure of FIG. 38;

FIG. 40 is a cross-sectional view of the storage structure of FIG. 38;

FIG. 41 is a cross-sectional view of the end elevational view of FIG. 39;

FIG. 42 is a side elevational view of the storage structure of FIG. 38 further including a conduit;

FIG. 43 is a side elevational view of two copies of another embodiment of a storage structure useable in the system depicted in FIG. 33 for holding a flexible container for containing biopharmaceutical material;

DETAILED DESCRIPTION

In accordance with the principles of the present invention, systems and methods for freezing, storing and thawing biopharmaceutical materials are provided.

In an exemplary embodiment depicted in FIGS. 1–6, portions of a system for cooling, freezing, preserving, processing, transporting, thawing, and storing biopharmaceutical materials are shown. The system may include a sterile container, such as a flexible container 10, adapted to contain the biopharmaceutical materials and adapted to be supported by a supporting structure, such as a frame 15. Flexible container 10 and frame 15 may also be adapted to be received in a temperature control unit 20, a transportation device 290 (FIGS. 13 and 14), and/or a storage unit.

Flexible container 10 may be formed of a laminated film which includes a plurality of layers and may have an interior volume ranging from 0.01–100 liters, for example. Further, flexible container 10 could be available in a variety of sizes to accommodate different uses, for example, 5, 10, and 20 liter flexible containers may be utilized. Also a biocompatible product-contacting layer of the interior of flexible container 10 may be formed of a low density polyethylene, very low density polyethylene ethylene vinyl acetate copolymer, polyester, polyamide, polyvinylchloride, polypropylene, polyfluoroethylene, polyvinylidenefluoride, polyurethane or fluoroethylenepropylene, for example. A gas and water vapor barrier layer may also be formed of an ethylene/vinyl alcohol copolymer mixture within a polyamide or an ethylene vinyl acetate copolymer. Further, flexible container 10 may include a layer with high mechanical strength (e.g. a polyamide), and an external layer with insulating effect to heat welding, for example, polyester. The layers may be compatible with warm and cold conditions and may be able to withstand ionizing irradiation for sterilization purposes. Also, flexible container 10 may have a large surface area to volume ratio, and a relatively thin wall thus promoting heat transfer therethrough when received in temperature control unit 20. One example of materials useful for formulation of flexible container 10 is described in U.S. Pat. No. 5,988,422 to Vallot, the entire subject matter of which is hereby incorporated herein by reference. Also, flexible container 10 may be disposable, thus promoting ease of use and preventing cross-contamination of the interior of flexible container 10 which might result when reusing other types of containers.

Figure 2:
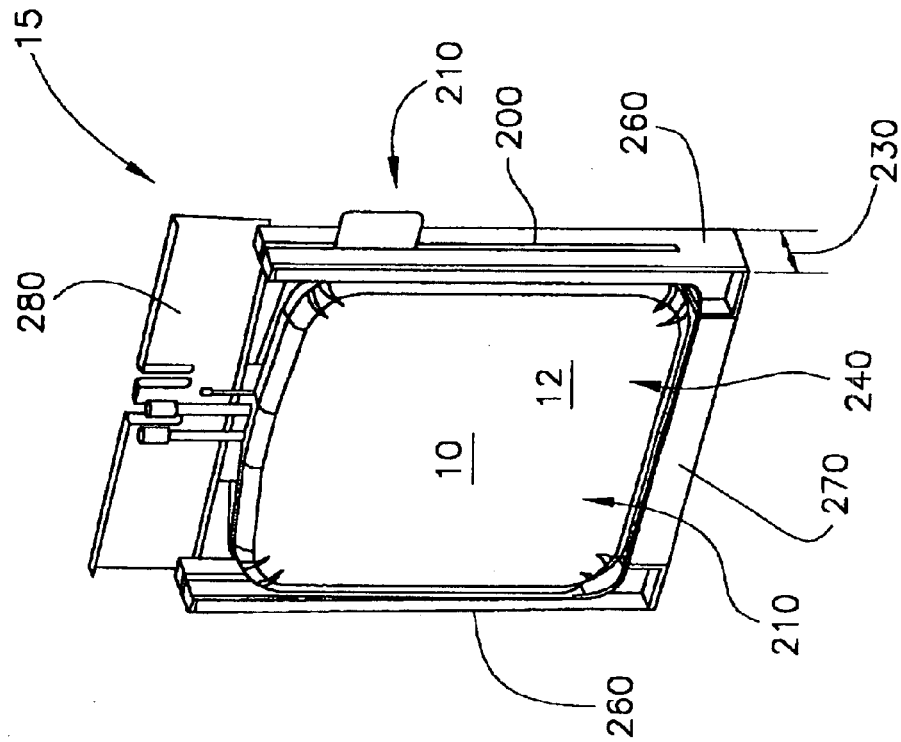
FIG. 2 is a perspective view of the flexible container of FIG. 1 received in a frame.
Figure 1:
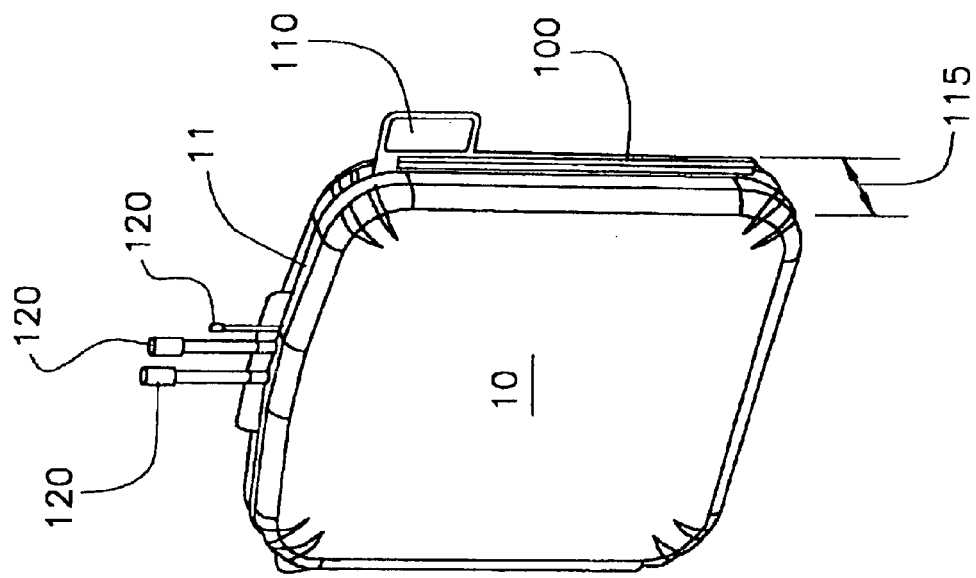
FIG. 1 is a perspective view of a flexible container in accordance with the present invention.

Sterile, flexible container 10 may be adapted to be received in frame 15 for supporting flexible container 10. For example, flexible container 10 may include an outwardly-extending flange 100 adapted to be received in a channel 200 of frame 15, as depicted in FIGS. 1–3. For example, flange 100 could be a plastic reinforcement rod dimensioned to be received in channel 200. Thus, flange 100, and therefore flexible container 10, may be inserted vertically downward or removed vertically upward, but may not be moved laterally or in directions other than up and down due to the engagement of flange 100 with channel 200. Thus, flange 100 serves to support the flexible container 10 laterally, retain a shape of flexible container 10 during filling thereof, reduces sagging of container 10 and ensures dimensional stability of flexible container 10 by spreading a load placed thereon along three different sides of flexible container 10, i.e., both sides and the bottom thereof.

Further, flexible container 10 may include a vertically extending flange or rod (not shown) projecting from a top side 11 of flexible container 10. The vertically extending flange may be configured to be received in channel 200 and may be substantially perpendicular to flange 100. The vertically extending flange also may be configured to connect to a top portion of frame 15 to reduce sag of flexible container 10 when flexible container 10 is received in frame 15.

Flexible container 10 may also include a tab 110 or other means for receiving a label to provide an indication to a user as to the contents of flexible container 10. Such a label may include written information, an embedded microchip, a RF transmitter and/or an electronic or magnetic bar code for indication of the contents of flexible container 10 to facilitate identification, tracking, and/or characterization of the contents thereof. The use of the label may thus simplify management of materials stored in flexible container 10, received in frame 15, when it is stored in a large freezer containing other frames and flexible containers which may appear similar thereto.

As shown in FIG. 2, flexible container 10 may include one or more ports or conduits 120 to allow filling or draining of biopharmaceutical materials or other solids, liquids, or gases into and/or out of interior (not shown) of flexible container 10. Conduits 120 may also be used to insert a measurement probe (not shown) inside flexible container 10 (e.g., a pH electrode, a conductivity sensor, temperature probe, an ion selective electrode, a spectophotometric probe, an ultrasound sensor, an optic fiber.) Conduits 120 may be positioned in the top part of the container and/or in the bottom part of flexible container 10. The position of the conduits may facilitate filling and/or drainage of the containers. Conduit 120 may be integral to flexible container 10 or it may be connectable to a receiving port (not shown) thereof For example, conduit 120 could be connected to a receiving port using a fitting placed within the inlet port. Fittings such as those described in U.S. Pat. No. 6,186,932, may be used for the connection of such conduits. Also, fittings which can maintain the sterility of the contents of the container or flexible container may preferably be used. The fittings may be configured in different shapes, such as straight fittings and/or angled fittings including ninety (90) degree elbows, if desired. In another example, conduit 120 may include a filter (not shown) to filter any impurities or other undesirable materials from the biopharmaceutical material.

Figure 6:
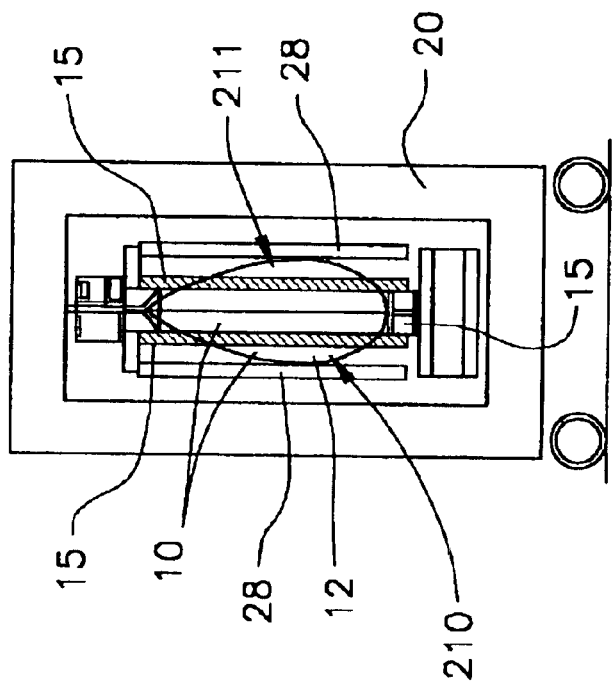
FIG. 6 is a side cross-sectional view of the temperature control unit of FIG. 5.
Figure 5:
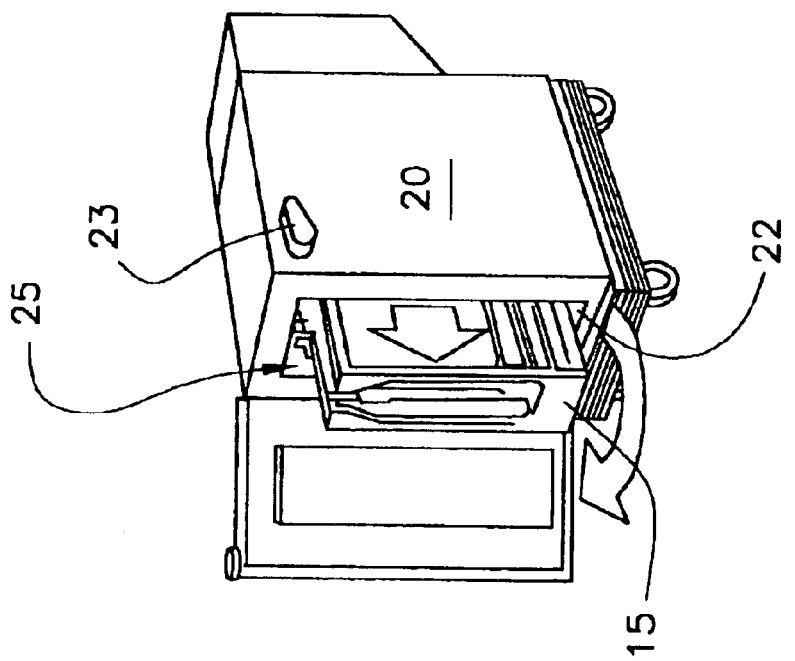
FIG. 5 is a perspective view of a temperature control unit receiving the frame and flexible container of FIG. 2 therein.

Temperature control unit 20 is configured to control the temperature of an interior 25 thereof, as depicted in FIGS. 5–6. Also, temperature control unit 20 may include therein, or may be coupled to, a controller (not shown) to allow a user to control the heating, cooling, freezing or thawing, for example, of the biopharmaceutical materials in flexible container 10, when it is inserted into interior 25 of temperature control unit 20. Heating, cooling, freezing or thawing of the contents of flexible containers 10 placed inside temperature control unit 20 may be controlled by blowing a continuous stream of cold or warm air, by direct contact of the containers with cold or warm surfaces, or by spraying cooling fluid (e.g., liquid nitrogen), for example.

In a preferred embodiment, temperature control unit 20 is a heat exchanger having one or more conduction plates for heating and/or cooling flexible container 10 and biopharmaceutical materials contained therein, as depicted in FIGS. 5–6. For example, temperature control unit 20 may include plates 28 for contacting flexible container 10 to cool the contents thereof. Also, one or more of plates 28 may be moveable to allow compression of flexible container 10 when flexible container 10 is received in frame 15 and frame 15 is received in interior 25 of temperature control unit 10. Further, temperature control unit 20 may include one or more non-temperature controlled walls (not shown) separate from plates 28 which may be configured to compress flexible container 10, when flexible container 10 is received in frame 15 and frame 15 is received in interior 25 of temperature control unit 20, as depicted in FIG. 6.

Frame 15 may be formed to receive and support flexible container 10 to provide additional rigidity and support to flexible container 10, thus facilitating handling, storage, and/or temperature control thereof. Frame 15 may include a first opening 210 and a second opening 211 (FIG. 6) on an opposite side of frame 15 from opening 210. These openings expose a large surface area of flexible container 10 to interior 25 of the temperature control unit 20. Through these openings, flexible container 10 may contact heat transfer surfaces such as plates 28 (FIG. 6), air at a controlled temperature, or liquid cooling spray within temperature control unit 20. For example, a first side 12 of flexible container 10 may contact a heat transfer surface (e.g., one of plates 28) of interior 25 of temperature control unit 20 (FIG. 5) through opening 210 to control the temperature of the biopharmaceutical material in flexible container 10. Alternatively, side 12 of flexible container 10 may be exposed to a still or circulating air within the temperature control unit 20. For example, the biopharmaceutical material may be frozen or thawed while in flexible container 10, when flexible container 10 is received in frame 15 and frame 15 is received in temperature control unit 20.

Also, flexible container 10 may be adapted to be compressed by plates 28, (FIG. 6), when substantially filled with the biopharmaceutical material, and flexible container 10 and frame 15 are received in interior 25 of temperature control unit 20. Further, the contents of flexible container 10 may be frozen or solidified while plates 28 are compressing it in temperature control unit 20 to cause flexible container 10 to have a dimension or width 115 in a direction between first opening 210 and second opening 211 (FIG. 6) of frame 15, which is less than or equal to a dimension or width 230 of an interior 240 of frame 15 in the same direction as dimension 115. Thus, flexible container 10 having the biopharmaceutical material frozen therein may be confined within an envelope or thickness defined by frame 15. By compressing flexible container 10 in frame 15, a substantially rectangular cross-sectional profile is created of flexible container 10 having the biopharmaceutical material therein. Such a cross-sectional profile promotes contact between flexible container 10 and heat transfer plates 28. This is particularly true in the corners of flexible container 10, thus allowing freezing to proceed in a uniform manner in a direction normal to plates 28. Further, the compression of flexible container 10 may force the biopharmaceutical material in flexible container 10 to occupy any voids or spaces between plate 28 and flexible container 10. By reducing or minimizing such voids or spaces, contact of plate 28 with flexible container 10 may be more uniform and thus cause more uniform cooling of the biopharmaceutical material contained in flexible container 10.

Frame 15 may further include upwardly extending sides 260, a bottom 270 and a top 280 to protect and support flexible container 10. Top 280 may be hingedly attached to frame 15 allow top 280 to be opened and allow flexible container 10 to be inserted into interior 240, and top 280 may be closed to protect flexible container 10. Also, top 280 may include a handle 285, as best depicted in FIG. 4, and top 280 may be releasably connectable to sides 260. Thus, a user may connect top 280 to sides 260 to allow handle 285 to be gripped to carry frame 15 with or without flexible container 10 received therein, which may contain biopharmaceutical material. Frame 15 may preferably be formed of materials which remain stable and retain their structural properties. Specifically, such materials should retain their load-bearing capacity and exhibit glass transition temperatures no higher than negative 80 degrees Celsius while being resistant to cleaning agents and methods commonly used in biopharmaceutical manufacturing, e.g., sodium hydroxide, sodium hypochloride (CLOROX), peracetic acid, etc.

For example, sides 260 may be formed of fluoropolymer resin (i.e. TEFLON) and top 280 and bottom 270 may be formed of stainless steel. Also, sides 260, bottom 270 and/or top 280 may be made of any number of other materials including aluminum, polyethylene, polypropylene, polycarbonate, and polysulfone, for example. Further materials may include composite materials such as glass-reinforced plastic, carbon-fiber reinforced resins, or other engineering plastic materials known to offer high strength-to-weight rations and which are serviceable at various temperatures of interest. It will be understood by those skilled in the art that sides 260, bottom 270 and/or top 280 may be monolithic and integrally formed as one piece or suitably connected together. Further, sides 260, bottom 270 and/or top 280 could be formed of a same material (e.g. stainless steel) or they could be formed of different materials and connected together. Frame 15 may also include one or more foot members 14 for maintaining frame 15 in an upright position, as depicted in FIG. 5. As will be understood by those skilled in the art, foot members 14 may be integral to or connectable to one or more sides 260 of frame 15.

Figure 8:
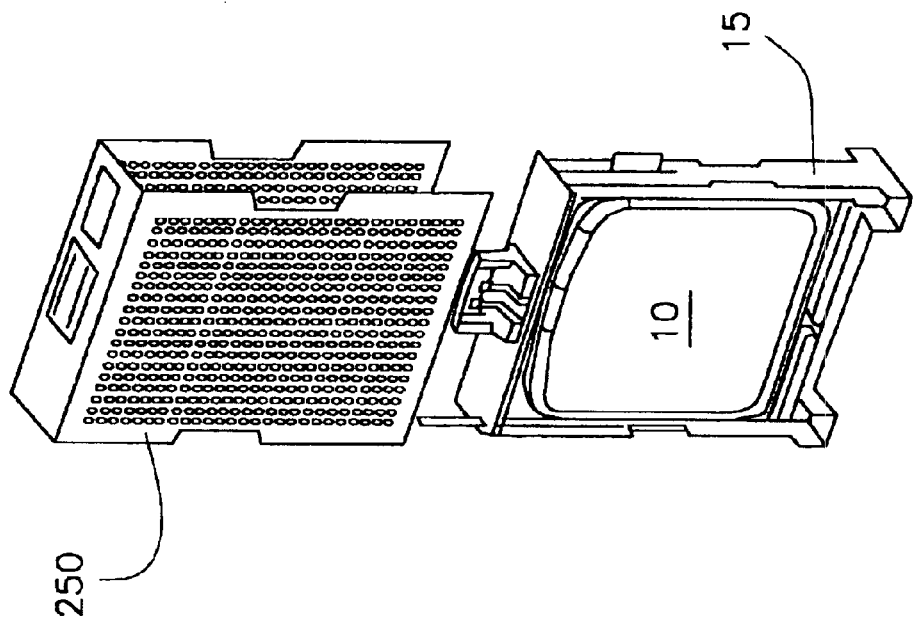
FIG. 8 is perspective view of the frame and the flexible container of FIG. 4 receivable in a protective cover.
Figure 7:
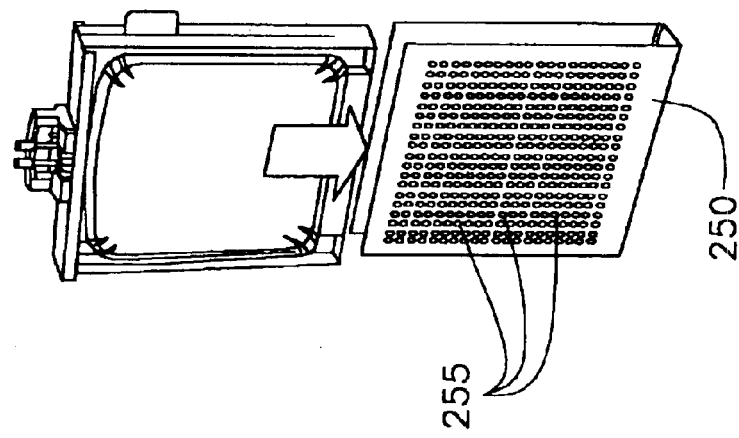
FIG. 7 is perspective view of the frame and the flexible container of FIG. 2 receivable in a protective cover.
Figure 9:
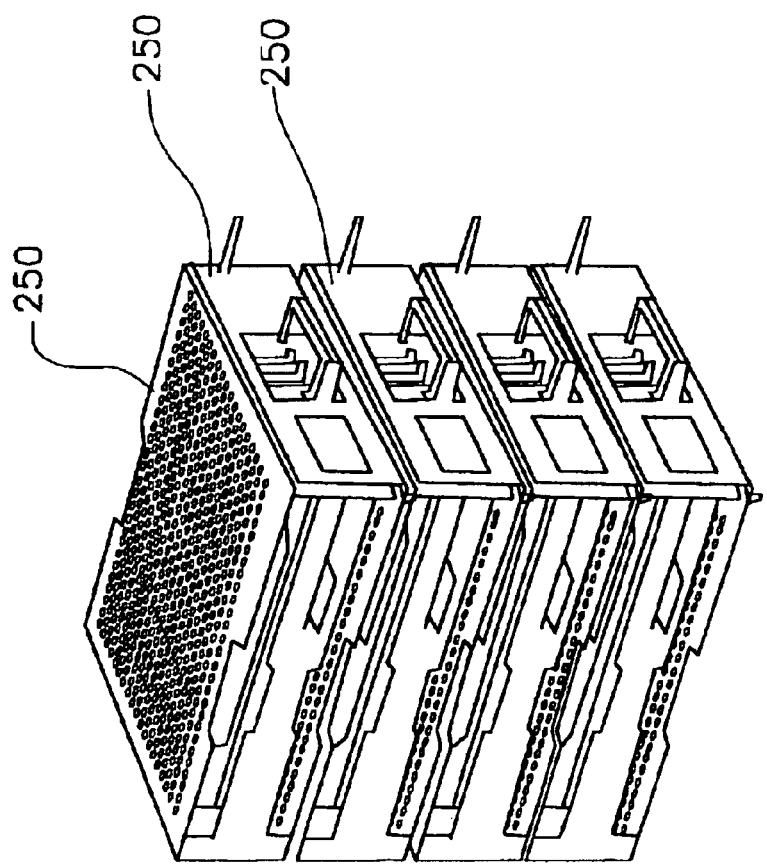
FIG. 9 is a perspective view of a plurality of the flexible containers and frames received in protective covers of FIG. 8 being stacked one atop another.

Further, frame 15 may be adapted to be received in a protective structure or cover 250 to protect flexible container 10, as depicted in FIGS. 7 and 8. Protective cover 250 may cover opening 210 and/or second opening 211 to protect flexible container 10, when flexible container 10 is received in frame 15, from being punctured or otherwise damaged. Further, protective cover 250 may also include a plurality of apertures 255 to facilitate heat transfer therethrough, when flexible container 10, frame 15, and cover 250 are received in temperature control unit 20 (FIG. 5) or another controlled temperature environment, such as a walk in freezer. Apertures 255 also allow a visual control of the interior of the flexible container 10, when protective cover 250 covers frame 15. Two or more frames 15 enclosed in protective cover 250 are stackable horizontally or vertically, as depicted in FIG. 9, for example. In both situations, intimate contact between adjacent faces of stacked cases may be prevented by wedges (not shown) to permit unhindered passage of air. This arrangement is favorable for the rapid and uniform control of the temperature when interior 25 of temperature control unit 20 is cooled or heated by convective air effect. Protective cover 250 also allows flattening of liquid filled flexible containers to a thickness defined by interior surface of protective cover 250 for more efficient storage and handling. Further, cover 250 may be configured to receive flexible container 10 from the top thereof or the bottom thereof, as is evident from FIGS. 7 and 8, respectively.

Figure 10:
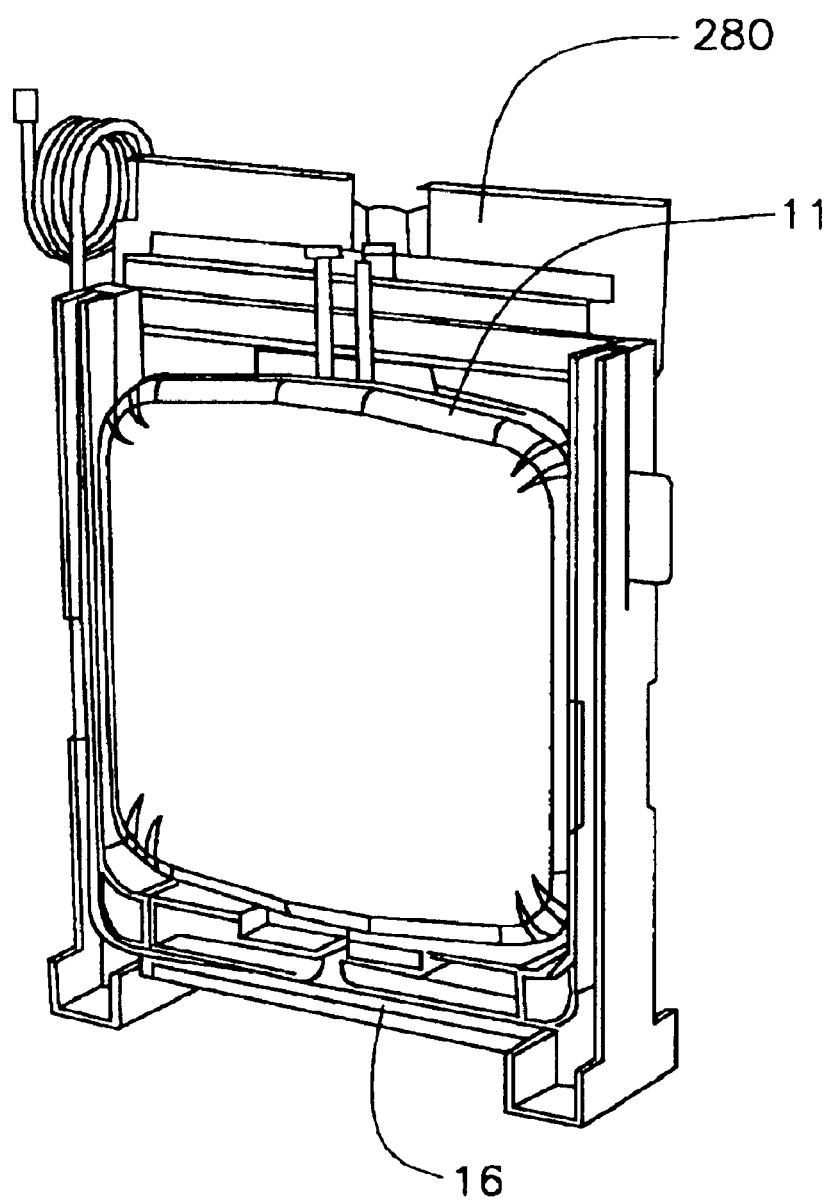
FIG. 10 is a perspective view of the frame and the flexible container of FIG. 2 showing a channel for receiving drain tubing connectable to the flexible container.
Figure 12:
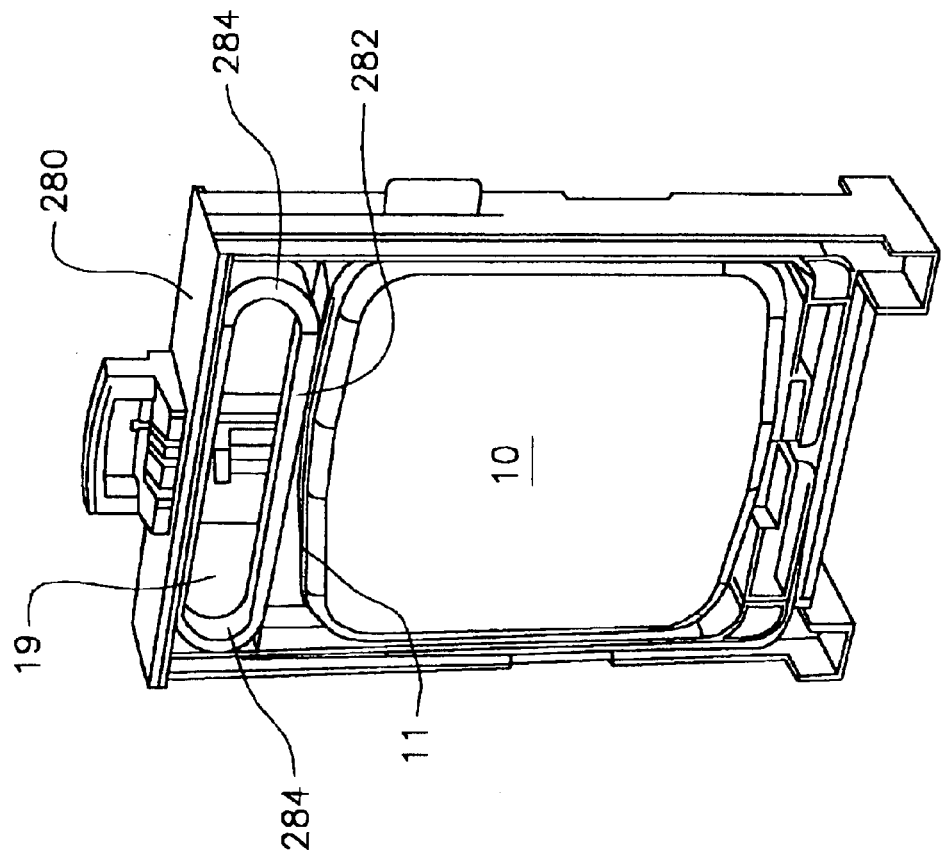
FIG. 12 is a perspective view of the frame and the flexible container of FIG. 2 including drain tubing receivable in a cavity between the flexible container and the top of the frame.
Figure 11:
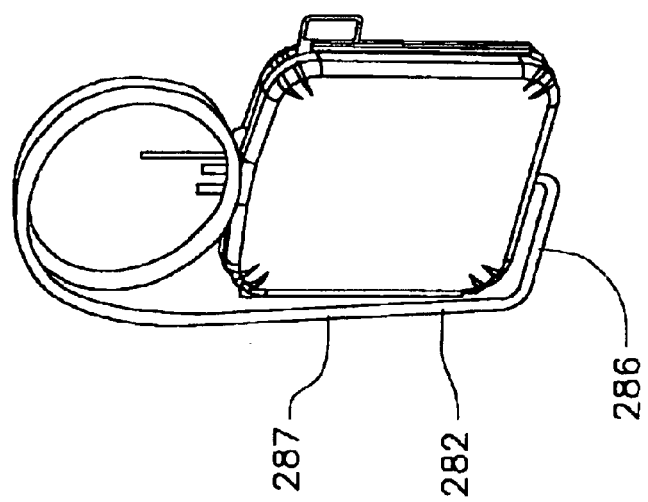
FIG. 11 is perspective view of the flexible container of FIG. 2 connected to drain tubing receivable in the channels of FIG. 10.

Frame 15 may also hold ancillary equipment and tubing. For example, as depicted in FIG. 10, frame 15 may be equipped with a channel 16 along one or more of sides 260 and/or bottom 270 to route drain tubing 282 (FIGS. 10–12). Flexible container 10 may be connected to or integral to drain tubing 282 which may be configured to be received in channel 16, that is, it may include a horizontally extending portion 286 and a vertically extending portion 287 to conform to the horizontal and vertical portions of channel 16, as depicted in FIG. 11. A compartment or cavity 19 may be located between top 11 of flexible container 10 and top 280 of frame 15, as depicted in FIG. 12. Cavity 19 may receive drain tubing 282 for storage prior to using drain tubing 282 to drain the interior of flexible container 10. Further, cavity 19 may include capstans 284, around which drain tubing 282 may be wrapped for storage thereof. Cavity 19 may also be used to support flexible container accessories such as vent filters, online filters, connectors and sampling ports (not shown). Cavity 19 may provide protection of the accessories during storage and transportation. The accessories are often made of plastic that can become brittle at low temperatures. Cavity 19 may secure the accessories in a safe position thus inhibiting the accessories from moving away from frame 15 and flexible container 10 and being damaged or ruptured.

Figure 14:
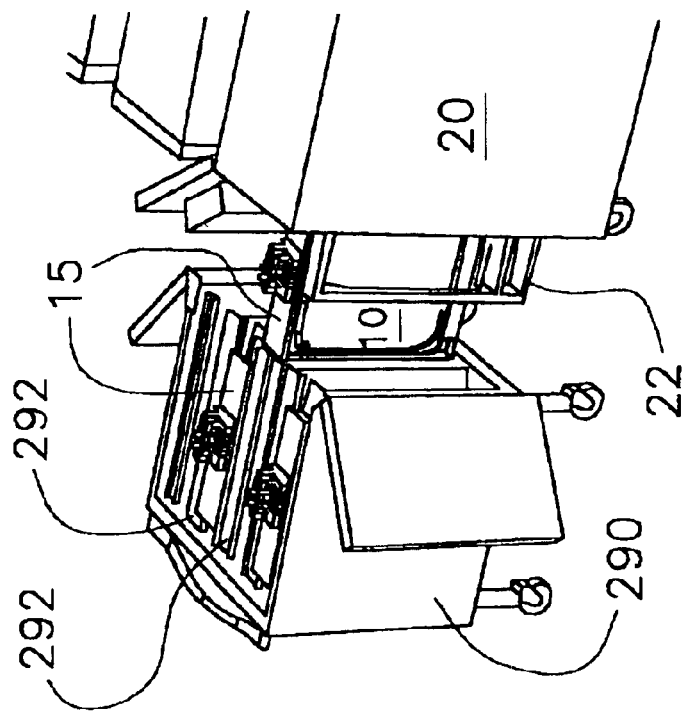
Figure 13:
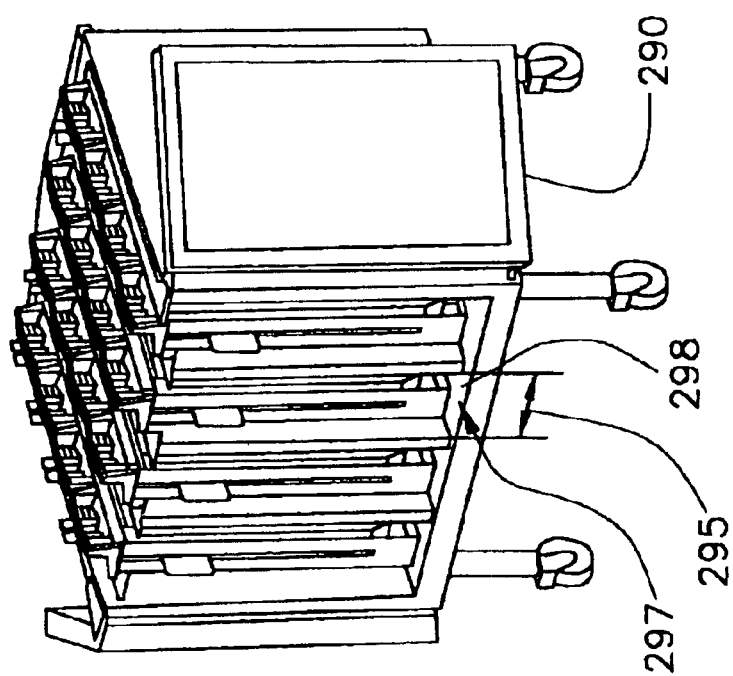
FIG. 13 is perspective view of a cart device for transporting one or more of the frames and flexible containers of FIG. 2.

Moreover, frame 15 may be adapted to be received in a storage unit or a transportation device, such as a cart 290, as depicted in FIGS.13–14. For example, width 230 of frame 15 may be less than or equal to a dimension or width 295 of a channel 297 of cart 290 to allow frame 15 to be received in cart 290. Also, a bottom side 298 of channel 297 may be at a same or similar height as a bottom side of interior 25 of temperature control unit 20, as depicted in FIGS. 5 and 13–14 to allow frame 15 to be easily slid from cart 290 to interior 25 of temperature control unit 20. Further, temperature control unit 20 may also include a moveable support 22 for holding frame 15 in interior 25 of temperature control unit 20. Moveable support member 22 may also be advanced outside of interior 25 with frame 15 supported thereon. Thus, moveable support member 22 may be advanced to a point wherein frame 15 may be slid off moveable support member 22 into channel 297 of cart 290. Also, channel 297 may include one or more channel supports 292 for supporting frame 15 in channel 297.

Temperature control unit 20 may also include a frame advancing mechanism to advance frame 15 outside of interior 25 of temperature control unit 20, which may be activated by a lever 23, as depicted in FIG. 5. For example, the frame advancing mechanism may include movable support member 22 being advanced in response to activation of lever 23. Thus, frame 15 may be easily moved from interior 25 of temperature control unit 20 to cart 290 through movement of moveable support member 22 holding frame 15, when temperature control unit 20 and cart 290 are located adjacent to each other. Cart 290 may have insulated walls for reducing heat losses during storage or transportation of frame 15 holding one or more flexible containers 10. In addition, for long term storage of the biopharmaceutical product contained in flexible container 10, in either a liquid or a frozen state, a walk-in, a chest or a cabinet chiller or freezer (not shown) can be equipped with rails or channel supports (not shown) adapted to receive frames 15.

Frame 15 may secure flexible container 10 in a defined position. Such arrangement facilitates the handling and transportation of liquid filled flexible container 10. In particular, the filling and drainage operation are facilitated by the self-standing position of flexible container 10 supported by frame 15, when supported by foot members 14. Alternatively, flexible container 10 may be filled and/or drained while frame 15 having flexible container 10 therein is located inside cart 290. Classically, liquid filled flexible containers are drained by gravity. Flexible containers are usually hung upside down or at least tilted to permit a complete drainage. This operation may be unsafe and/or cumbersome due to weight constraints, for example, for flexible containers with volumes higher than 10 liters. Thus, it may be desirable to hold higher volume containers in self-standing frames to facilitate drainage thereof.

In another embodiment of the present invention, a flexible container 350 for holding biopharmaceutical material therein may be adapted to be received in a frame 360 for supporting flexible container 350, as depicted in FIGS. 15–19. Frame 360 may include a left side 370, a right side 380, a bottom side 390 and a top 400 connectable to each other. Flexible container 350 may include a flange 405 and frame 360 may include one or more projections or posts 420 projecting outwardly from top 400 of frame 360 in a direction substantially perpendicular to left side 370 and right side 380. Flange 405 may include one or more apertures 410 dimensioned to receive one or more posts 420. Specifically, the one or more posts 420 may be inserted though the one or more apertures 410 and post(s) 420 may thus support flange 405, and thus, flexible container 350 and any contents therein. One or more capture flanges or members 430 may further be attached to top 400, may be hingedly rotatable toward flexible container 350, and may be adapted to receive one or more posts 420. Thus, when capture member 430 is rotated toward flexible container 350 and posts 420 are received therein, posts 420 may provide support to flexible container 350 in a vertical direction while capture member 430 may inhibit or prevent movement of flange 405 of flexible container 350 in a direction parallel to posts 420 and away from top 400 (e.g., a horizontal direction). Therefore, such support in the vertical direction may inhibit sagging of container 350 and such support in the horizontal direction may inhibit container 350 from moving away from frame 360 and being damaged by a foreign object, for example.

Flexible container 350 may also include one or more tie-down loops 450 connectable to frame 15 via tie-down bosses 460 (FIG. 19), on an exterior surface 385 of right side 380 and on an exterior surface (not shown) of left side 370, for example. Left side 370 and/or right side 380 may also include apertures 470 (FIGS. 15 and 19) to allow tie-down loops 450 to pass therethrough for attaching to tie-down bosses 460. By connecting tie-down loops 450 to tie-down bosses 460, flexible container 350 may be secured on its bottom side portions, thus inhibiting flexible container 350 from moving away from frame 360 and being damaged or ruptured by a foreign object, for example.

Figure 15:
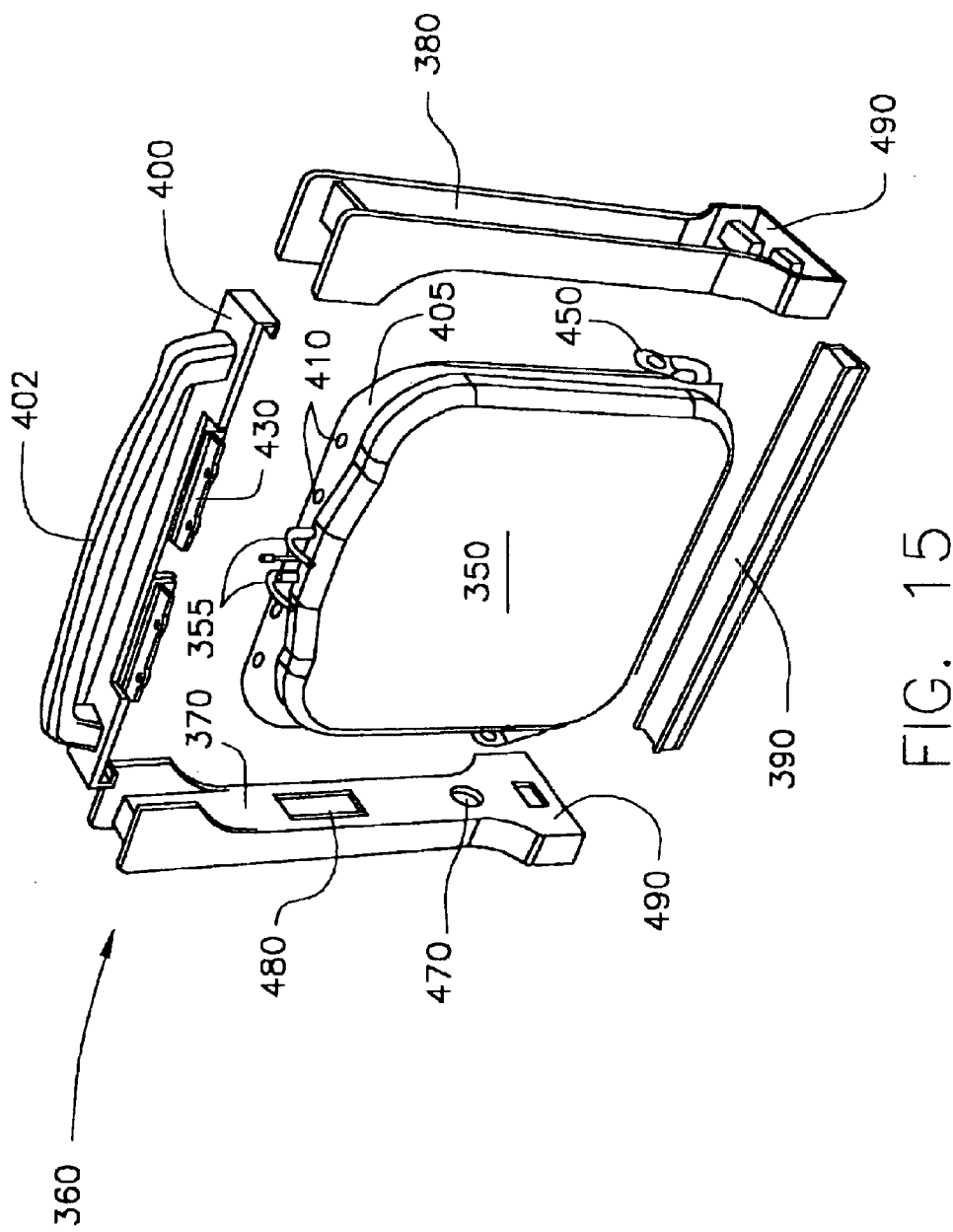
FIG. 15 is a exploded view of another embodiment of a flexible container for holding biopharmaceutical materials, receivable in a modular frame, in accordance with the present invention.
Figure 17:
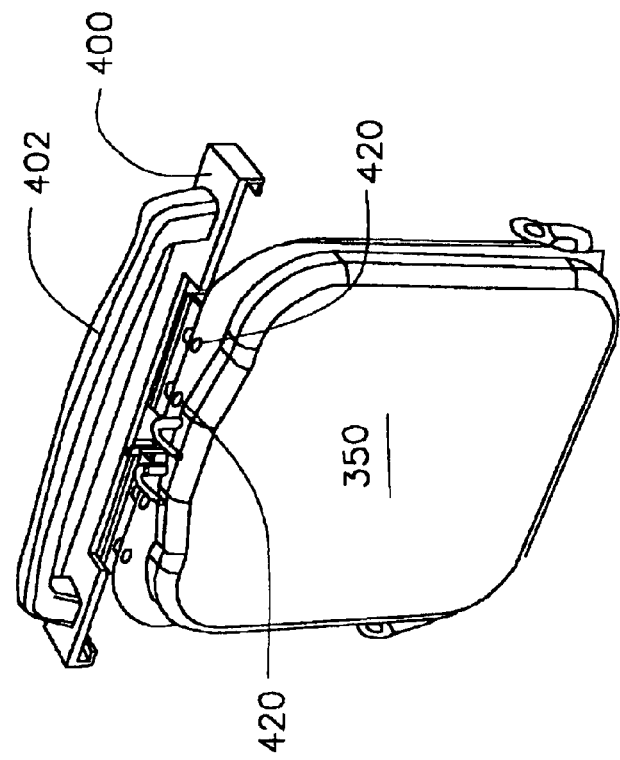
FIG. 17 is a perspective view of the flexible container of FIG. 15 connected to the top handle of the frame of FIG. 15.
Figure 16:
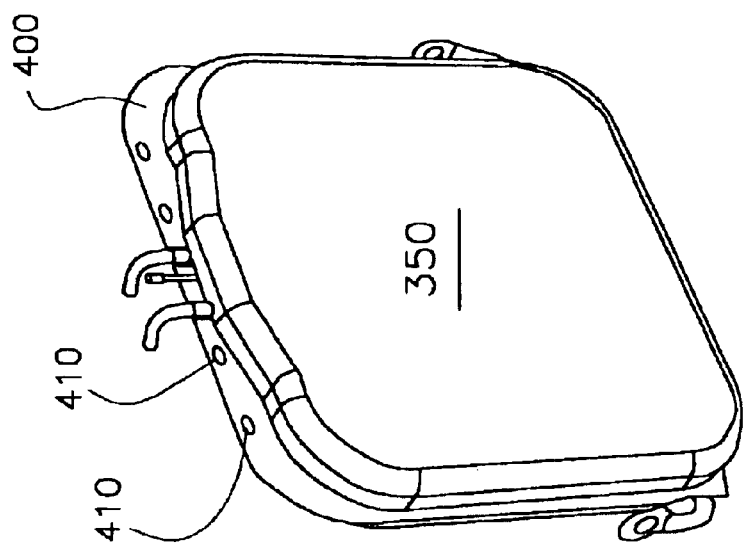
FIG. 16 is a perspective view of the flexible container of FIG. 15.

Also, flexible container 350 may include one or more ports or conduits 355 to allow insertion or extraction of biopharmaceutical liquids or other liquids or gases into and/or out of an interior (not shown) of flexible container 350. Referring to FIG. 15, frame 360 may include a translucent or transparent portion 480 to allow a user to view a label (not shown) or other indication to a user as to the contents of flexible container 350, when such a label or indicator is attached to flexible container 350. The label could include written information, an embedded microchip, a RF transmitter, and/or an electronic or magnetic bar code, for example. Further, transparent portion 480 could further include a fiberoptic guide/reader or a waveguide, for example. Left side 370 and/or right side 380 may also be formed to include one or more foot members 490 for maintaining frame 360 in an upright position. As will be understood by those skilled in the art, foot members 490 may be integral to or connectable to left side 370 and/or right side 380.

Top 400 may include a handle 402 to allow a user to carry flexible container 350, when flexible container 350 is received in frame 360, with or without flexible container 350 being substantially filled with biopharmaceutical material. Top 400 may also be adapted to be connected to flexible container 350 to allow top 400 to support flexible container 350, without flexible container 350 being connected to left side 370 right side 380, or bottom side 390, as depicted in FIG. 11. Thus, a user may carry flexible container 350 connected only to top 400.

Figure 20:
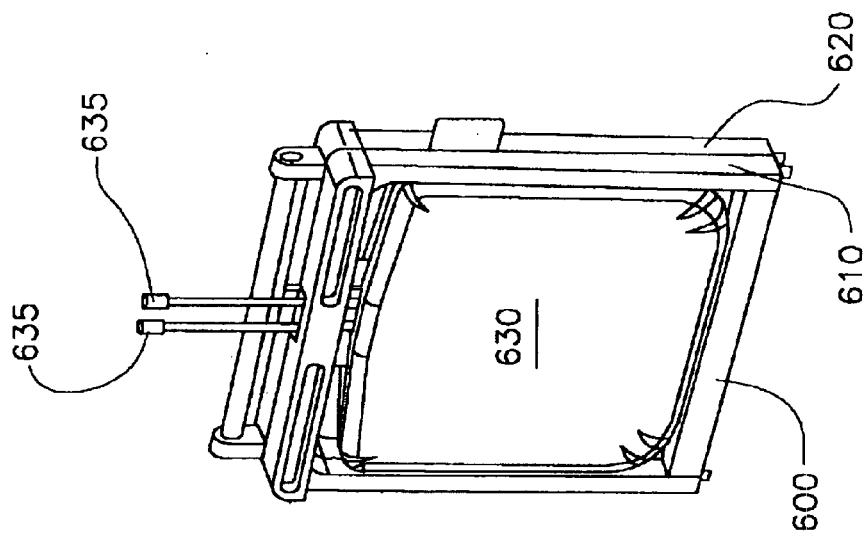
FIG. 20 is a perspective view of yet another embodiment of a flexible container for storing and freezing biopharmaceutical materials being received in a clamping frame, in accordance with the present invention.
Figure 18:
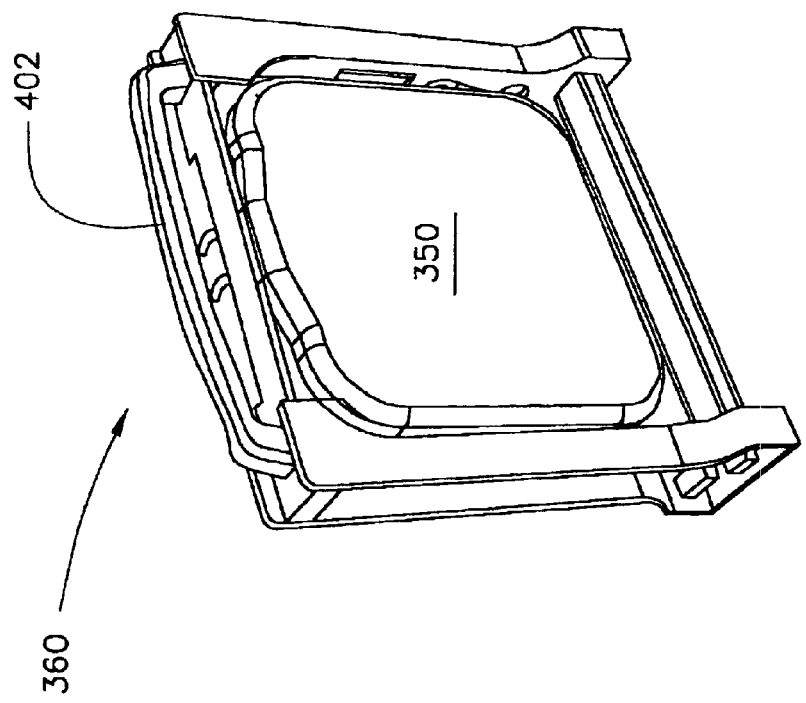
FIG. 18 is a perspective view of the flexible container received in the frame of FIG. 15.

In another embodiment of the present invention, a frame 600 may include a first portion 610 and a second portion 620 adapted to be connected or clamped to one another, as depicted in FIGS. 20–22. By connecting to one another, first portion 610 and second portion 620 also may secure flexible container 630 for holding biopharmaceutical materials there between. Specifically, flexible container 630 may include one or more flanges 660 which are connectable between an interior surface 615 of first portion 610 and an interior surface 625 of second portion 620. Flanges 660 may include one or more apertures 665 for receiving posts 670 projecting from interior surface 625 of second portion 620. Interior surface 615 of first portion 610 may also include one or more apertures corresponding to posts 670. The receiving of posts 670 in apertures 615 inhibits movement of flange 660, and thus flexible container 630, when flange 660 is received between first portion 610 and second portion 620. Thus flexible container 630 may be held between first portion 610 and second portion 620 such that lateral and/or vertical support is provided to flexible container 630 by first portion 610 and second portion 620 in conjunction with posts 670. Thus, flexible container 630 may retain its shape during filling thereof, reduced sagging of flexible container may be achieved, and flexible container 630 may be contained within an envelope of space defined by frame 600.

Flexible container 630 may include one or more ports or conduits 635 to allow filling or draining of biopharmaceutical liquids or other liquids or gases into and/or out of an interior (not shown) of flexible container 630. Flexible container 630 may also include a tag or label 680 protruding from frame 600 to indicate to a user the contents of flexible container 10, when such a label or indicator is attached to flexible container 630. Also, a pivoting side 612 of first portion 610 may be openable to allow flexible container 630 to overhang a bottom side 614 of first portion 610, when flexible container 630 is not substantially filled with biopharmaceutical material. This allows flexible container 630 to be extended to minimize slack or wrinkles in flexible container 630, during filling thereof After flexible container 630 is substantially filled with biopharmaceutical material, any slack in flexible container 630 may be taken up and flexible container 630 may not overhang bottom side 614. Thus, pivoting side 612 may be closed, when flexible container 630 is substantially filled with the biopharmaceutical material, to protect a bottom portion of flexible container 630 from contact with any external objects.

Figure 24:
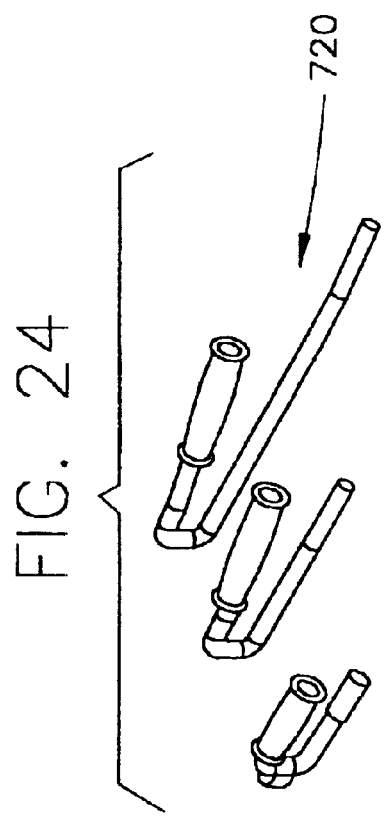
FIG. 24 are perspective views of various support rods for receiving different capacity flexible containers.
Figure 23:
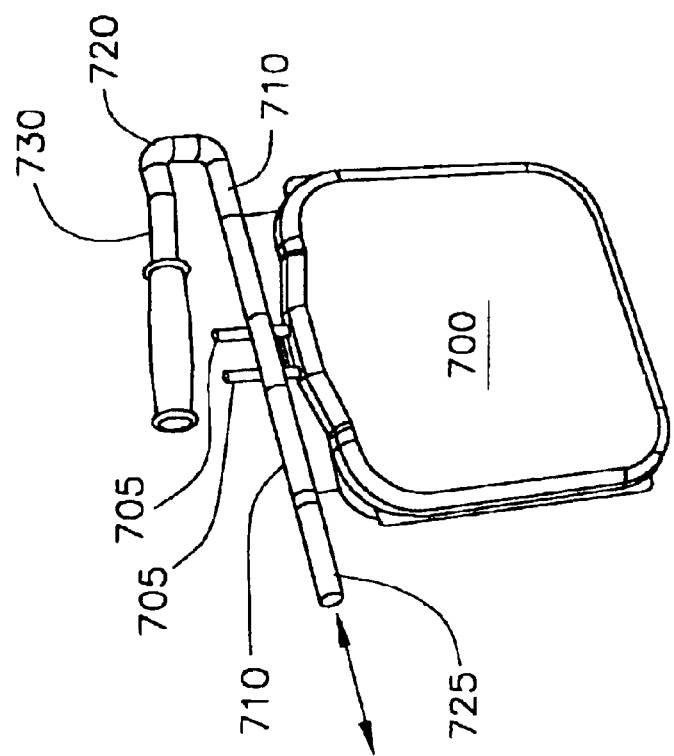
FIG. 23 is a perspective view of yet a further embodiment of a flexible container for storing and freezing biopharmaceutical materials wherein the flexible container receives a support rod, in accordance with the present invention.
Figure 26:
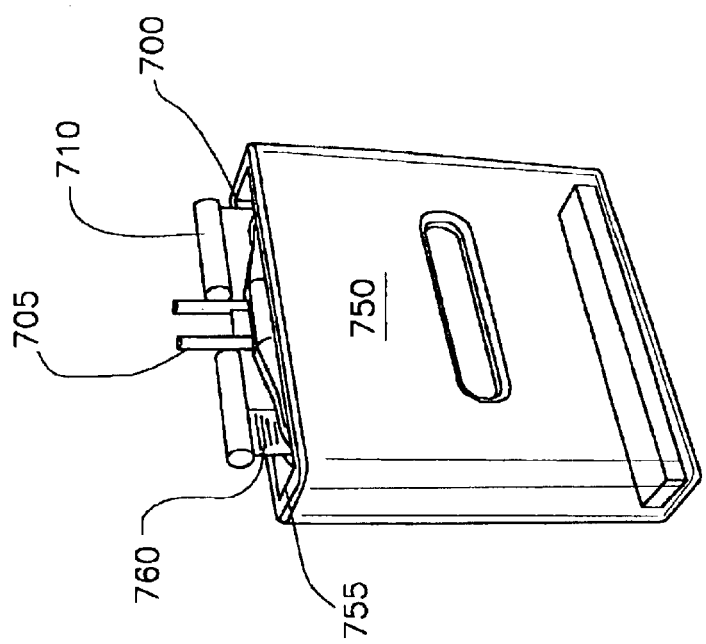
FIG. 26 is a perspective view of the flexible container of FIG. 23 being received in a protective cover, in accordance with the present invention.
Figure 25:
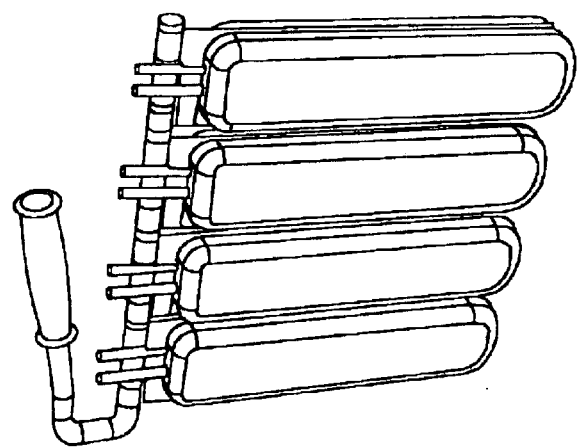
FIG. 25 is a perspective view of one of the support rods of FIG. 24 being received in the sleeves of a plurality of flexible containers for storing and freezing biopharmaceutical materials.

In a further embodiment of the present invention, a flexible container 700 for holding biopharmaceutical materials may include one or more sleeves 710 for receiving a support member 720 for supporting flexible container 700, as depicted in FIGS. 23–25. Specifically, sleeves 710 may be dimensioned to allow support member 720 to pass coaxially therethrough and support member 720 may include a supporting rod or lance portion 725 and a grip portion 730. Also, grip portion 730 may be formed such that it is located over the center of gravity of flexible container 700, when flexible container 700 is substantially filled with biopharmaceutical materials. Flexible container 700 may be carried by a user holding grip portion 730, for example, when flexible container 700 is substantially filled with liquid biopharmaceutical materials. Further, support member 720 may be adapted to hold more than one flexible container 700, as depicted in FIG. 25. Also, flexible container 700 may be received in a protective cover 750, as depicted in FIG. 26. Protective cover 750 may include an inner foam liner to inhibit or prevent shock or rupturing of flexible container 700. Also, protective cover 750 may be insulated to maintain flexible container 700 at a desired temperature. Further flexible container 700 may include a label 760, similar to label 110, to designate the contents of flexible container 700, which may protrude above a top surface 755 of protective cover 750. Flexible container 700 may also include one or more ports or conduits 705 to allow biopharmaceutical materials or other materials to be inserted therein or removed therefrom.

Figure 27:
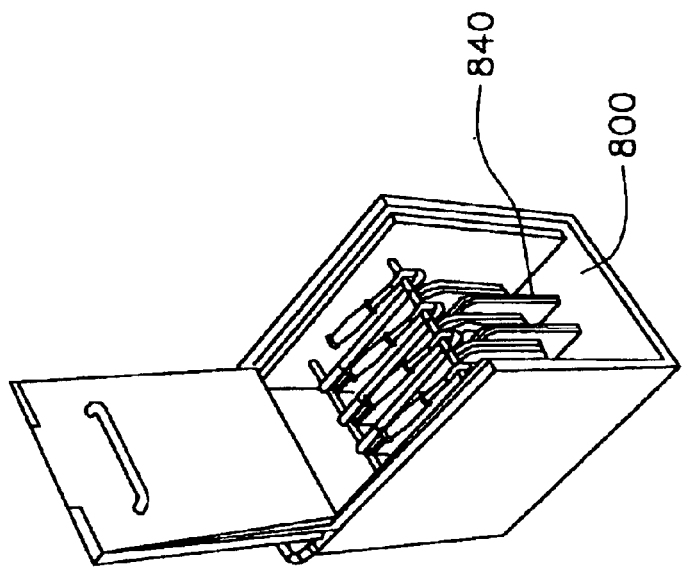
FIG. 27 is a perspective view of the flexible container and support rod of FIG. 24 being received in a cart device for transporting one or more of the flexible containers.
Figure 28:
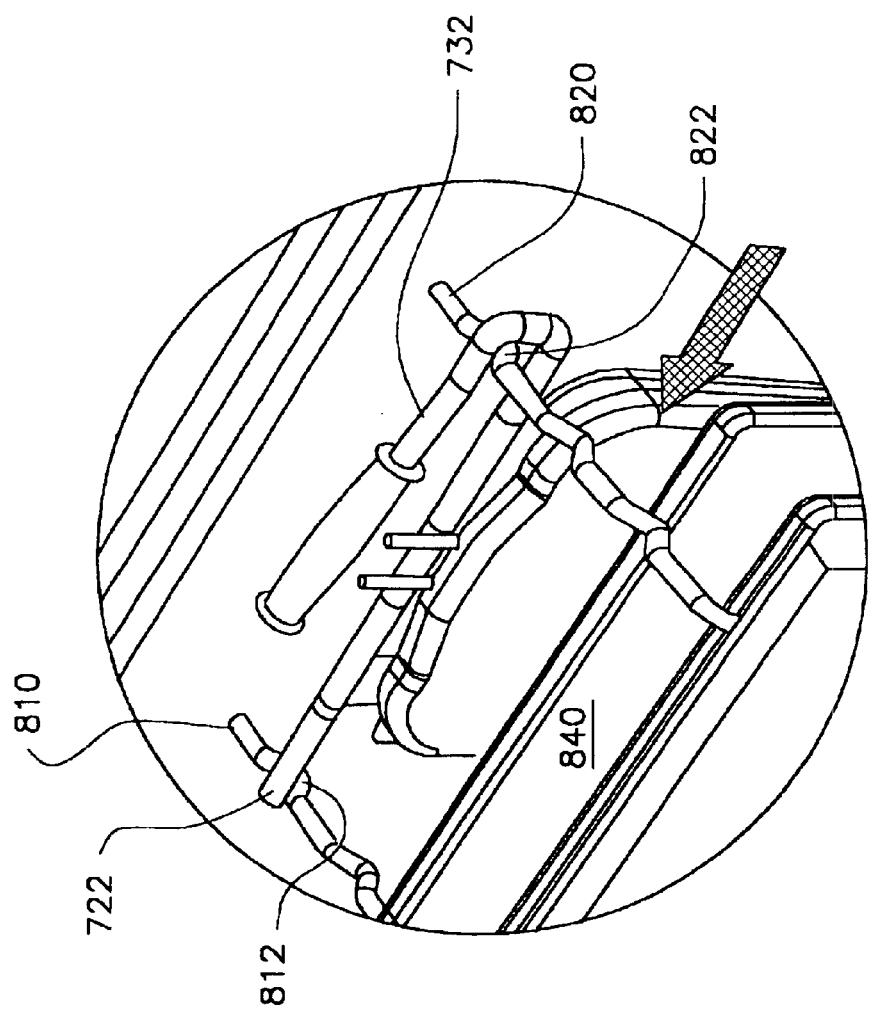
FIG. 28 is an enlarged perspective view of a portion of FIG. 27 depicting the flexible container and support rod of FIG. 23 being received in the cart of FIG. 27.
Figure 29:
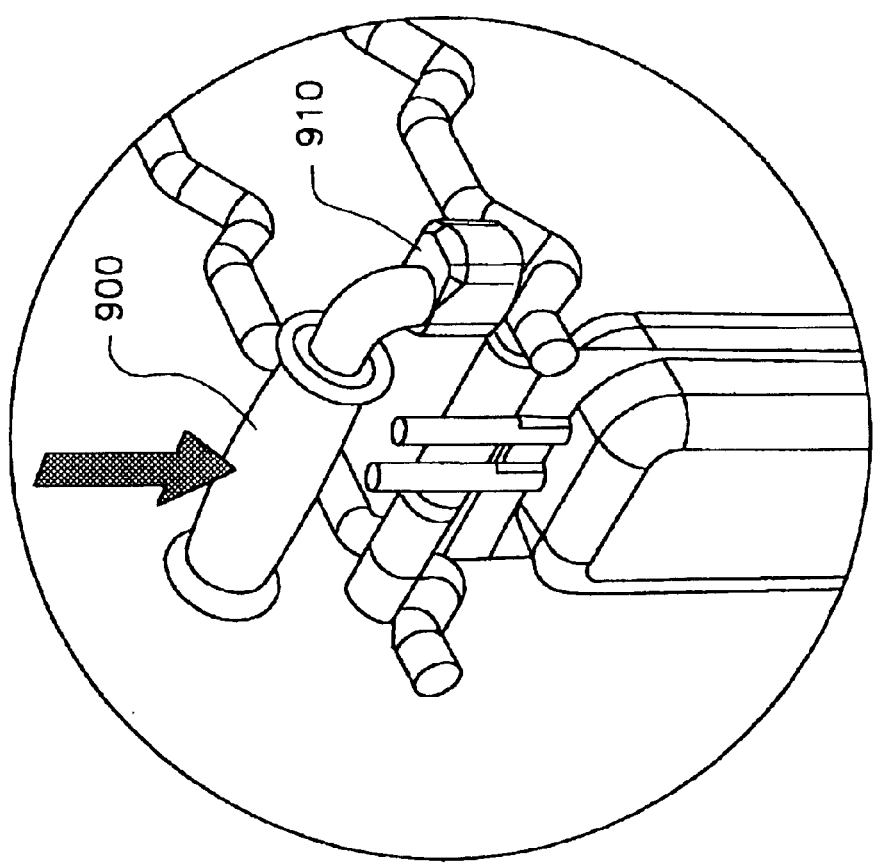
FIG. 29 is a perspective view of another embodiment of a support rod being received in a sleeve of a flexible container and the support rod being received on support members of a cart for transporting the flexible container, in accordance with the present invention.

As depicted in FIGS. 27–28, support member 720 may be received in a storage unit 800, while support member 720 supports flexible container 700, which is substantially filled with biopharmaceutical material, for example. Specifically, a first end 722 of support member 720 may be placed on top of a supporting frame 810 of storage unit 800 and a bottom side 732 of grip portion 730 of support member 720 may be placed atop a second supporting frame 820 of storage unit 800. Supporting frame 810 and second supporting frame 820 may include recessed portions 812 and 822, respectively, to receive support member 720. Thus, as is evident from FIG. 28, supporting member 720 with flexible container 700 attached thereto may be easily slid into storage unit 800. Also, the sides of recessed portions 812 and 822 may inhibit movement of support member 720 along supporting frame 810 and second supporting frame 820 in a direction substantially perpendicular to a longitudinal direction of support member 720, while contained in storage unit 800. Further, storage unit 800 may also include dividers 840 between adjacent flexible containers 700 to inhibit contact between adjacent flexible containers which might result in damage to the flexible containers themselves or their contents. In another example, a support member 900 (FIG. 29), similar to support member 720, includes a toe element 910 connected thereto, which is adapted to be received in and to rest upon second supporting frame 820 such that support member 900 may be vertically inserted on top of supporting frame 810 and second supporting frame 820, instead of being slid onto supporting frame 810 and second supporting frame 820, as for support member 720.

Although the containers are described herein as flexible containers, the containers may be made of a semi-rigid material such as polyethylene or the like. Such a semi-rigid material may retain its shape and/or stand up by itself when empty and when filled with a biopharmaceutical material. An example of such a container could include a container similar to a standard plastic milk jug. Containers made of such similar semi-rigid materials may benefit from additional rigidity supplied by attachment to a frame, for example. Further, the containers whether formed of a flexible or semi-rigid material, contain outer surfaces which contact the interior surfaces (e.g., heat transfer plates) of a temperature control unit 20 so that there is direct contact between the cooled (e.g., to a subzero temperature) or heated interior surfaces of temperature control unit 20 and the outer surfaces of the container containing biopharmaceutical materials. Alternatively, the outer surfaces of the containers for holding the biopharmaceutical materials may be in contact with air flow in interior 25 of temperature control unit 20 to cause the cooling and/or heating of the containers having the biopharmaceutical materials therein to cause the temperature of the biopharmaceutical materials to be controlled.

The biopharmaceutical material in the flexible containers described above may thus be cooled or otherwise thermoregulated in temperature control unit 20 (e.g., to a subzero temperature). When such operation is completed, the flexible containers may be removed from temperature control unit 20 by removing the flexible containers and the frames, or other support structures which the flexible containers are received in or connected to, for example. The frames or other support structures holding the flexible containers may be stored in a large chiller or freezer with an interior air temperature of about negative 20 degrees Celsius, for example.

Figure 30:
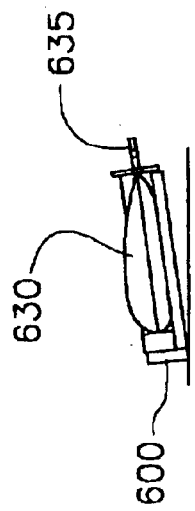
FIG. 30 is a side elevational view of the frame and flexible container of FIG. 20 configured to fill the container.
Figure 31:
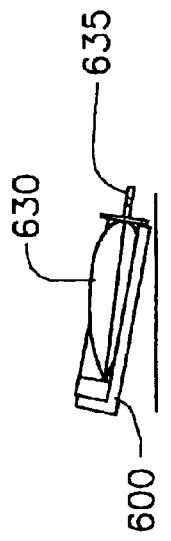
FIG. 31 is a side elevational view of the frame and flexible container of FIG. 20 configured to drain the container.
Figure 32:
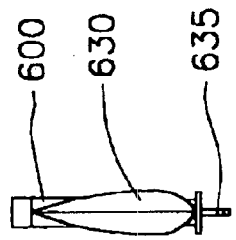
FIG. 32 is a side elevational view of the flexible container and frame of FIG. 20 configured to drain the container.

Also, the biopharmaceutical material in the flexible containers described above may be removed from and/or inserted therein by rotating the position of the flexible containers. For example, as depicted in FIG. 30, flexible container 630 received in frame 600 may be filled with liquid biopharmaceutical material through conduit 635 by rotating frame 600 such that conduit 635 is above a bottom side of frame 600. Also, flexible container 630 may also be emptied by turning frame such that conduit 635 is slightly below the bottom of frame 600, as depicted in FIG. 31, or by turning frame 600 upside down and allowing the contents to drain, as depicted in FIG. 32. The other flexible containers described above may be filled and/or drained through similarly manipulating the frames or support structures to which they are attachable.

A typical process of processing and/or preserving a biopharmaceutical material is described as follows. Flexible container 10 is inserted into frame 15 and top 280 is closed, as depicted in FIGS. 2–3. Biopharmaceutical material, for example liquid biopharmaceutical material, is inserted through conduit 120 into flexible container 10. Flexible container 10, while held in frame 15, is then inserted into temperature control unit 20, as shown in FIGS. 5 and 6, where the biopharmaceutical contents are frozen in a controlled manner (e.g., to negative 20 degrees Celsius or below), for example, such that the freeze rate (including the dendritic freeze front velocity from the sides of the container to the center) is controlled within upper and lower limits, as described in U.S. patent application Ser. No. 09/905,488, thus preventing or inhibiting cryoconcentration of the biopharmaceutical material, thereby preventing undesirable degradation of the biopharmaceutical material. After the biopharmaceutical material in flexible container 10 is frozen, flexible container 10 may be removed from the temperature control unit 20 and placed in a large freezer, for example, a walk-in freezer having an interior air temperature of about negative 20 degrees Celsius, as is typically present in large medical institutions (e.g., hospitals).

It will be evident to those skilled in the art from the above description that flexible container 350 (FIG. 15) may have its contents frozen or its temperature otherwise regulated and stored in the same manner as flexible container 10. Specifically, flexible container 350 may be received in frame 360 and frame 360 may be inserted into temperature control unit 20 or a different chiller, freezer or heater. Flexible container 630 (FIG. 20) may be received in frame 600, it may have its contents frozen in temperature control unit 20, and flexible container 630 may also be stored in a walk-in freezer. Similarly, flexible container 700 (FIG. 23) may receive supporting member 710 and it may be inserted into temperature control unit 20 or another means for heating or cooling its contents. Also, flexible container 700 may be stored in a walk-in freezer. From the present description, it will be further understood by those skilled in the art that modifications may be made to the specific examples described herein and the steps for performing the method for preserving, freezing, and/or processing the biopharmaceutical material.

Further, the above described flexible containers may be removed from a freezer or other system for storage of the flexible containers and contents thereof at a controlled temperature. These flexible containers having biopharmaceutical material therein may then be received in a controlled temperature control unit for heating, melting, and/or thawing the biopharmaceutical material contained in the flexible containers.

Figure 33:
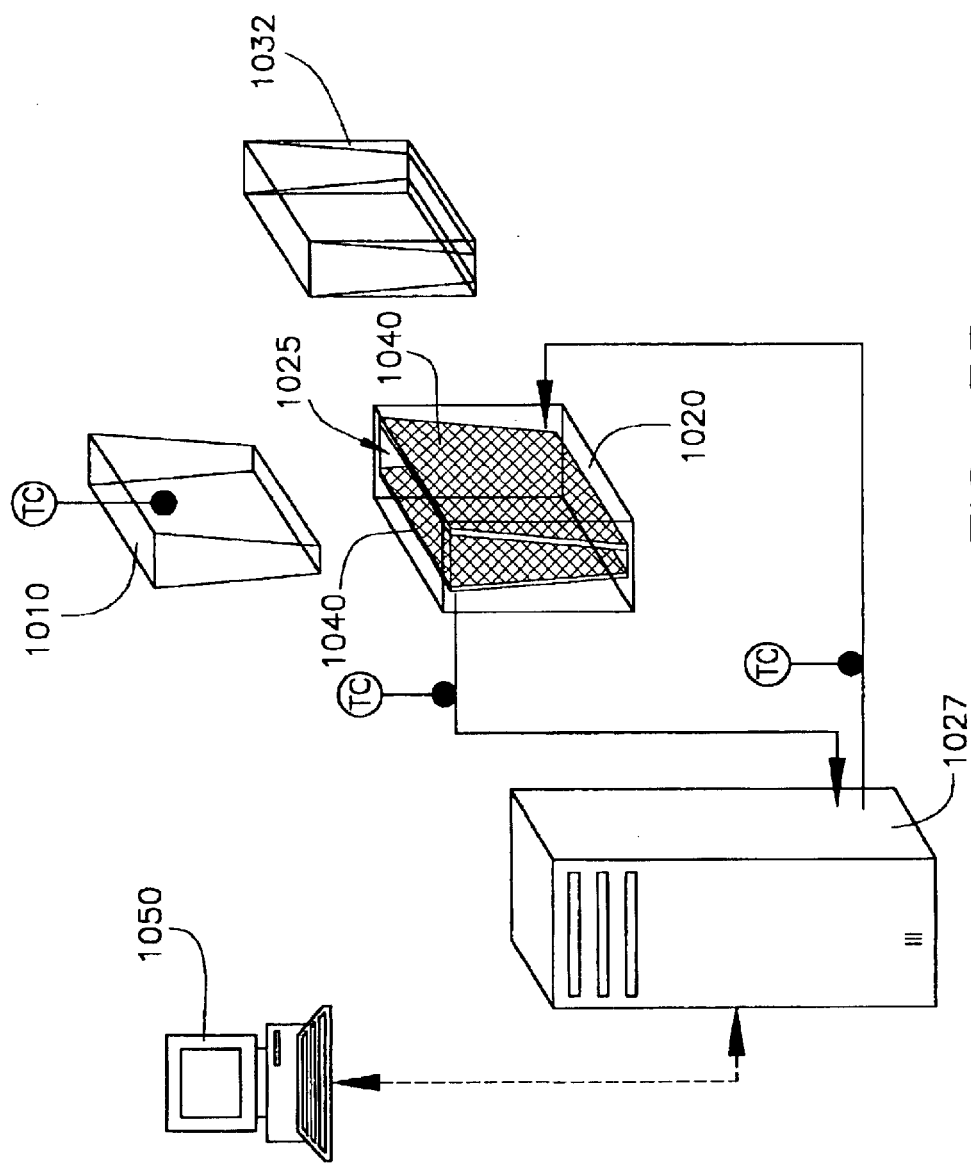
FIG. 33 is block diagram of another embodiment of a system for freezing, storing and thawing a biopharmaceutical material, in accordance with the present invention.

In another embodiment of the present invention, depicted in FIG. 33, a system for cooling, preserving and storing biopharmaceutical materials is shown. This system may include a sterile container such as a flexible container 1010 adapted to contain the biopharmaceutical materials, configured to conform to a shape of an interior of a temperature control unit 1020 ( e.g., a heat exchanger) and/or conform to a shape of an interior of a support structure 1032 for storing the biopharmaceutical materials.

Temperature control unit 1020 is configured to be operatively coupled to a temperature regulating unit 1027 for controlling fluid flow through a conductive medium, such as heat transfer plates 1040 of temperature control unit 1020 to control the temperature of an interior 1025 thereof. A controller 1050 allows a user to control temperature regulating unit 1027 to control heating and/or cooling of the conductive medium, such as plates 1040, to cause freezing or thawing, for example, of biopharmaceutical materials in a container such as flexible container 1010, when it is inserted into interior 1025 of temperature control unit 1020. Controller 1050 may also be coupled to a temperature sensor (not shown) located in interior 1025 of temperature control unit 1020. The temperature sensor may be located on one or more of plates 1040, for example, and may provide temperature feedback to controller 1050 to facilitate control of temperature regulating unit 1027. One example of a temperature control unit 1020 is described in co-owned U.S. patent application Ser. No. 09/905,488 filed Jul. 13, 2001, and co-owned U.S. patent application Ser. No. 09/863,126, filed May 22, 2001, the entirety of each of which is hereby incorporated herein by reference. The cooling systems described in the aforementioned applications, and freezing and/or thawing techniques described therein, may be used in conjunction with the systems and methods of freezing, storing and thawing biopharmaceutical materials of the present invention. Specifically, the cryogenic coolers or heat exchangers described in these applications may be configured to incorporate and/or receive the containers for storing biopharmaceutical materials described herein and any associated structures.

Flexible container 1010 may be configured to conform to the shape of interior 1025 of temperature control unit 1020. Specifically, flexible container 1010 may conform to interior 1025 such that any space or voids between flexible container 1010 and heat transfer plates 1040 might be reduced or prevented. For example, flexible container 1010 when substantially filled may form a parallelepiped shape. Further, flexible container 1010 may be configured such that it can conforms to shapes of interiors other than that of interior 1025 such that any spaces or voids between flexible container 1010 and heat transfer plates in such other shaped containers might be reduced or prevented. Although the containers are described herein as flexible containers, the containers may be made of a semi-rigid material. Such material may be used to construct a container which is shaped to conform to the interior of temperature control unit 1020. Preferably, the container whether formed of a flexible or semi-rigid material, contains surfaces which contact the interior surfaces (e.g., heat transfer plates) of temperature control unit 1020 so that there is direct contact between the cooled (or heated in a thawing process) surfaces of the temperature control unit and the outer surfaces of the container containing biopharmaceutical materials.

Figure 37:
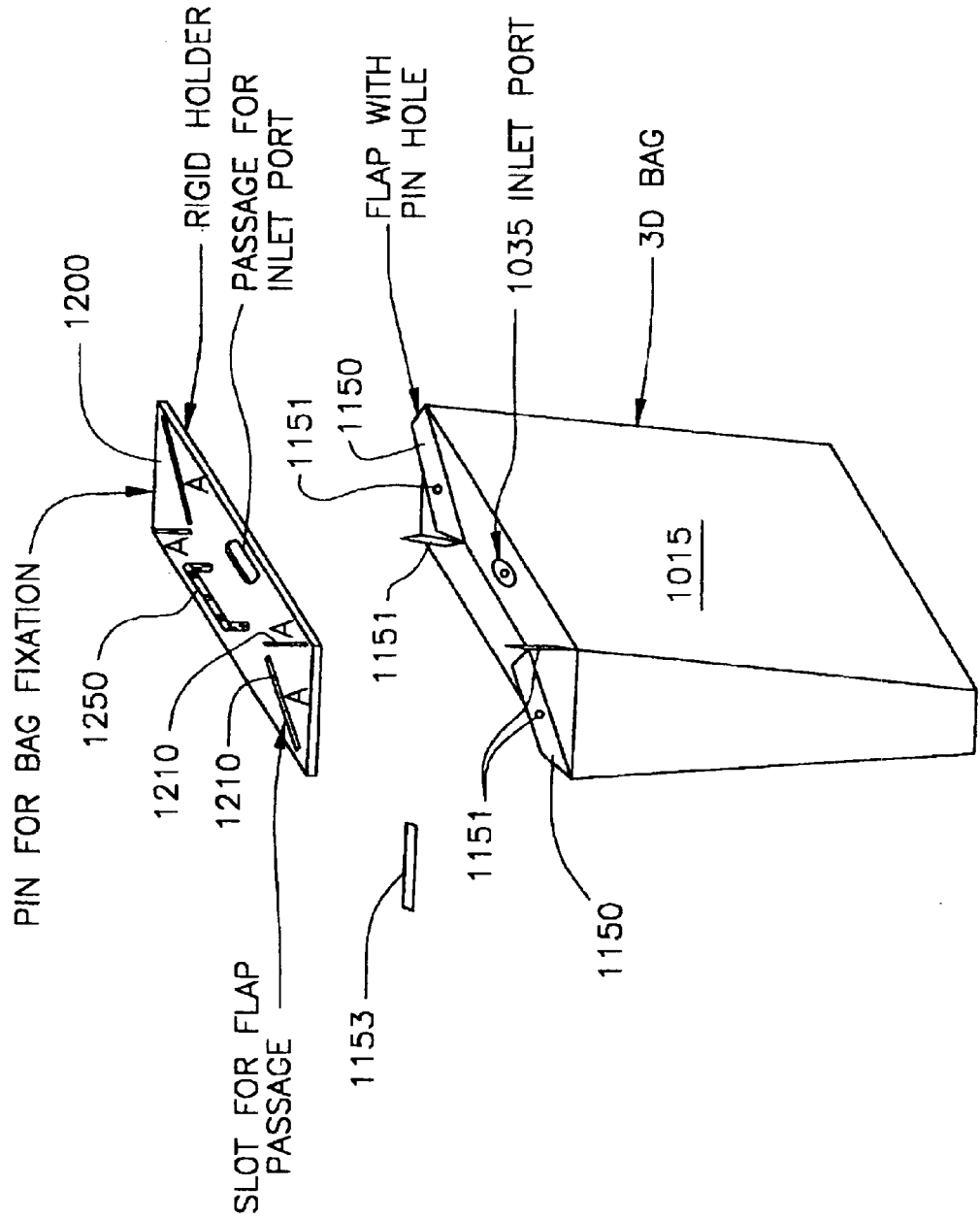
FIG. 37 is a perspective view of another embodiment of a container for storing and freezing biopharmaceutical materials including a sterile, flexible container and a rigid holder useable in connection with the present invention.
Figure 44:
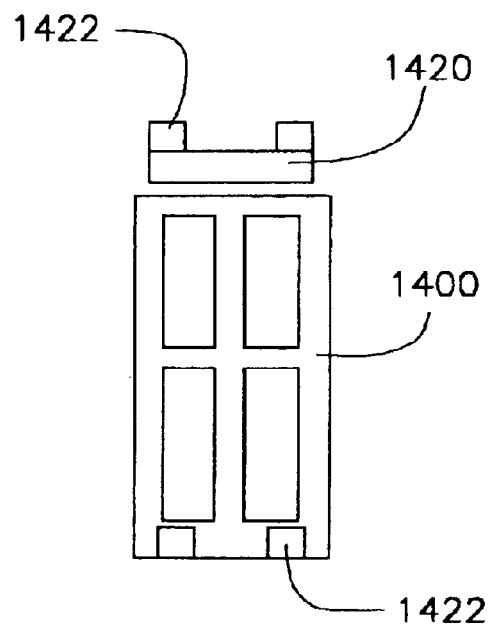
FIG. 44 is a side elevational view of the storage structure of FIG. 43.
Figure 46:
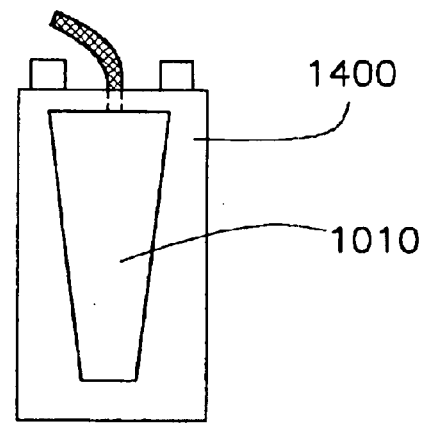
FIG. 46 is a side elevational view of the storage structure of FIG. 44, including the flexible container of FIG. 33 therein.
Figure 45:
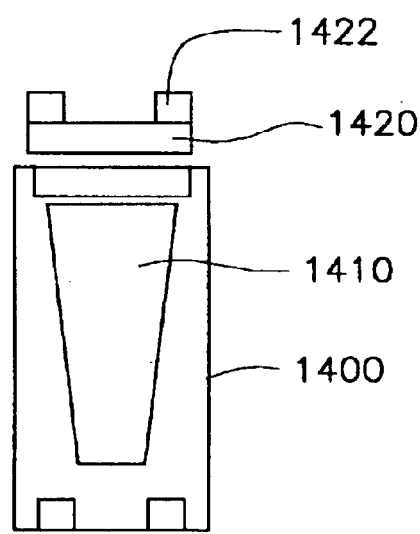
FIG. 45 is a side cross-sectional view of the storage structure of FIG. 44.

In one example, flexible container 1010 when substantially filled, may form a parallelepiped shape. Flexible container 1010 may be formed by welding of several sheets of material to form the parallelepiped shape, as depicted in FIGS. 36 and 37, among others. An example of a process for forming flexible container 1010 is depicted in FIGS. 34–36. A top film 1105 and a bottom film 1110, used to form the flexible container, are placed one atop another and an additional film 1115 and a film 1120 are pleated, for example, as bellows and inserted between film 1105 and film 1110. Four longitudinal welds are executed to seal the four longitudinal corners of the flexible container using flat heat welding. For example, 45 degree welds are performed between the inner bellows and top film 1105 and bottom film 1110 and transverse welds are performed to seal top and bottom faces of flexible container 1010. Flaps 1150 (FIG. 37) may be created by leaving a layer of film above the 45 degree welds. Also holes 1151 (FIG. 37) are made by die cutting in the flaps followed by circular film welding, as is known by those skilled in the art.

In another example, a flexible container 1015 used as a container for freezing, storing and thawing biopharmaceutical materials is depicted in FIG. 37. An inlet port 1035 allows biopharmaceutical materials to be inserted into an interior (not shown) of flexible container 1015 and to be removed therefrom. A tube (not shown in FIG. 37) similar to that shown in FIG. 42 may be connected to the inlet port 1035 using a fitting placed within the inlet port. Fittings such as described in U.S. Pat. No. 6,186,932, may be used for the connection of such tubes. Also maintain the sterility of the contents of the container or flexible container may preferably be used. The fittings may be configured in different shapes, such as straight fittings and/or angled fittings including ninety (90) degree elbows, if desired. A rigid or semi-rigid holder 1200 having holes 1151 may be inserted through slots 1210 in holder 1200. One or more pins 1153 may then be inserted through holes 1151. Thus, a user may hold and carry flexible container 1015 and holder 1200 by a handle 1250 of holder 1200. For example, each of four flaps 1150 may contain a hole 1151. The four flaps are insertable within each of the four slots 1210 on holder 1200. A pin may be inserted through each of the two holes on opposed slots. For example, long pins (not shown) may be inserted through a pair of holes in the flaps so that two pins may be used to support the holder 1200 to the flexible container 1015

Although pins are specifically mentioned herein, it will be understood by those skilled in the art that flexible container 1010 or another container may be used with or without holder 1200, and that other means of securing flexible container 1010 to the holder 1200 such as clamps, or other fastening systems may be used. Moreover, although the container is described herein as a flexible container, the container may be made of a semi-rigid material. Such material may be used to construct a container which is shaped to conform to the interior of temperature control unit 1020. Preferably, the container whether formed of a flexible or semi-rigid material, contains surfaces which contact the interior surfaces (e.g., heat transfer plates) of temperature control unit 1020 so that there is direct contact between the cooled (or heated in a thawing process) surfaces of the temperature control unit and the outer surfaces of the container containing biopharmaceutical materials.

Referring to FIGS. 38–42, a support structure such as a vessel 1060 may have an interior portion 1300 adapted to receive a container such as flexible container 1010 and a top 1310 for covering interior 1300. Interior portion 1300 is formed in a shape substantially similar to a container holding biopharmaceuticals, such as sterile, flexible container 1010, when filled or when containing the biopharmaceutical material. Thus, walls and/or bottom surface of interior portion 1300 may serve to support flexible container 1010, when flexible container 1010 containing biopharmaceuticals is inserted therein. Top 1310 may also include an aperture 1320 to receive a conduit or tube 1330 for filling and/or emptying flexible container 1010 therethrough, and through an inlet port of flexible container 1010 (not shown), as depicted in FIGS. 41–42. Aperture 1320 may include a filter (not shown) to filter any biopharmaceutical material. Flexible container 1010 in vessel 1060 may also be emptied by turning vessel 1060 upside down and allowing the contents to drain.

Vessel 1060, thus, may receive an empty, sterile, flexible container 1010. The flexible container 1010 may be filled via tube 1330 with biopharmaceutical material before flexible container 1010 is transferred to temperature control unit 1020 (FIG. 33). The flexible container may then be removed from vessel 1060 and placed into temperature control unit 1020 as shown in FIG. 33, wherein the cooling and freezing may occur. After the biopharmaceutical material is frozen (e.g., to negative 20 degrees Celsius or below) or its temperature otherwise regulated (e.g., thawed) in flexible container 1010 in temperature control unit 1020, flexible container 1010 may be returned to vessel 1060, for example. Vessel 1060 may be insulated to allow transportation of flexible container 1010 to a location for utilization of the biopharmaceutical material. Thus, in one embodiment of the system depicted in FIG. 33, support structure 1032 for receiving, transporting and storing a container such as a sterile flexible container 1010 comprises the insulated vessel depicted in FIGS. 38–42. However, if desired, vessel 1060 may not be insulated. Vessel 1060 may be constructed to efficiently be placed in a walk-in freezer or other structure for maintaining the biopharmaceutical material and flexible container 1010 in a frozen state or at an otherwise desirable temperature. Further, vessel 1060 may be adapted to receive a label or a tag 1340 which may include written information and/or an electronic or magnetic bar code for indication of the contents thereof to facilitate identification, tracking, and characterization of the contents thereof. The use of tag 1340 may thus simplify management of materials stored in vessel 1060 when it is stored in a large freezer containing other vessels which may appear similar thereto. For example, the freezer may be a walk-in freezer having an interior air temperature of about negative 20 degrees Celsius. In another example, flexible container 1010 may be placed in a separate rigid container (not shown), for example, an anodized aluminum container tapered to receive flexible container 1010 and configured to be placed into vessel 1060 and temperature control unit 1020 (FIG. 33) for freezing and/or thawing of the contents of flexible container 1010. The rigid container may be made of thermally conductive material and constructed to be stored in a large freezer when filled with biopharmaceutical material.

The bottom of vessel 1060 may contain one or more notches 1324 as depicted in FIGS. 38–42. The notches 1324 are configured to receive projections 1310 which are located on the top cover of the vessel 1060. When a top 1312 is placed on the vessel 1060, the projections allow for the stacking of one vessel on top of another vessel. The projections 1310 of a bottom vessel may fit into the notches 1324 located at the bottom of a vessel stacked on top thereof. The top cover of the each vessel 1060 may also contain a hole 1320 or other passage to allow for a tube 1330 connected to the container on flexible container 1060, to be placed therethrough. Such a configuration is depicted in FIG. 42.

Figure 47:
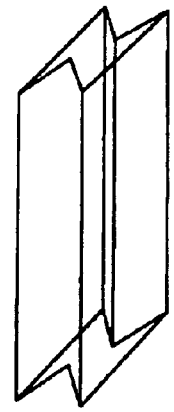
FIG. 47 is a perspective view of the storage structure of FIG. 44 being folded.

In another embodiment of the invention, support structure 1032 of FIG. 33 may be in the form of a foldable container such as a crate 1400 which is also adapted to receive flexible container 1010 such as that depicted in FIG. 33 within interior portion 1410, as depicted in FIGS. 43–46. Also, crate 1400 may be adapted to stack with vessel 1060 of FIGS. 33 and 38–42, or additional crates 1400 as depicted in FIGS. 43–47, wherein top 1310 and a top 1420 of vessel 1400 include projections 1422 and projections 1310, respectively. Vessel 1060 and crate 1400 include receiving ports 1424 and 1314, respectively, to receive the projections, thus allowing stacking of crate 1400 and/or vessel 1060. Crate 1400 (FIGS. 43–47) and/or vessel 1060 (FIGS. 38–42) might be formed of an expanded polystyrene, for example a STYROFOAM type material, a rigid polyurethane (closed cell), polyethylene, or other suitable engineering materials, including composites, for example. Further, crate 1400 and vessel 1060 may be formed via injection-molding, extrusion blow molding, or injection blow molding, for example. As depicted in FIG. 47, crate 1400 may be foldable or collapsible to allow storage thereof in a less voluminous manner. As such a collapsible crate 1400 and/or vessel 1060 may also be formed, for example, of polycarbonate, polysulfone, polyethylene, or other suitable engineering materials, including composites, for example. Such a foldable collapsible crate 1400 may also be formed via injection-molding, or machining and assembly of component parts thereof.

Figure 48:
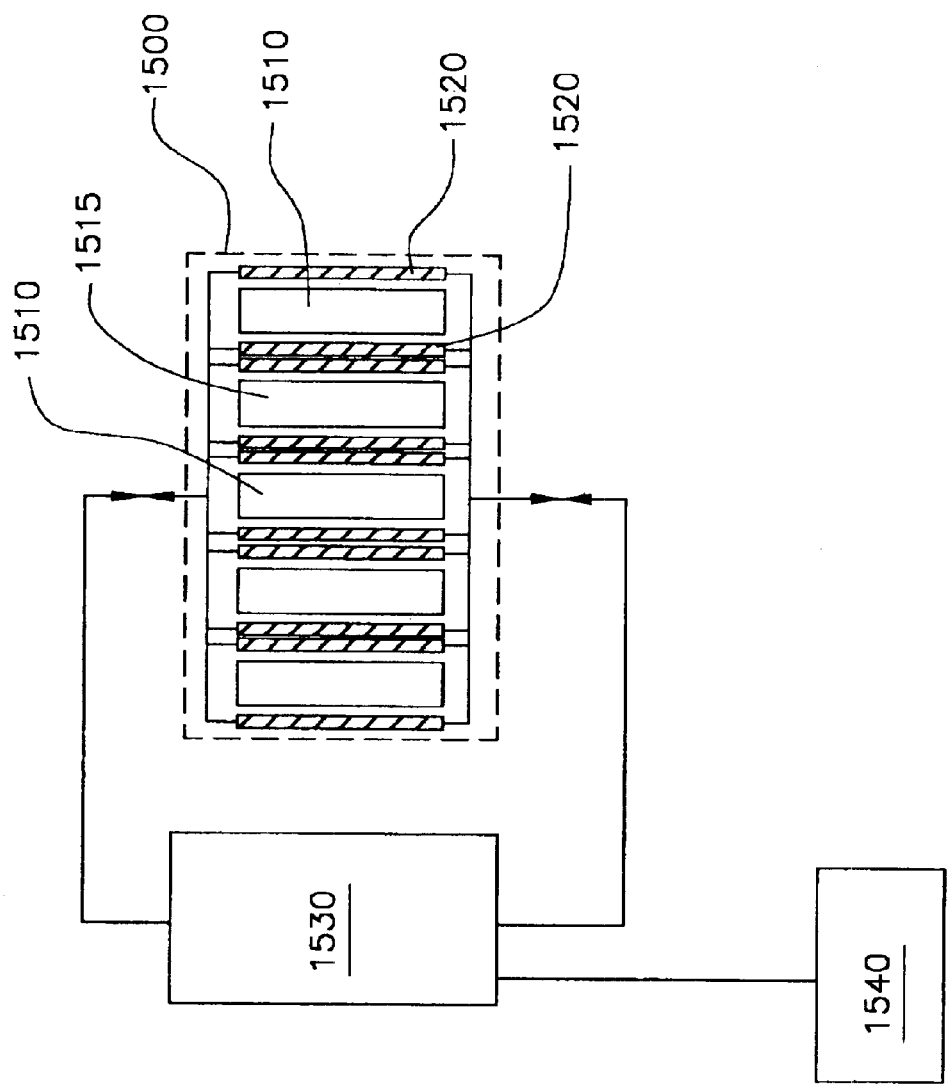
FIG. 48 is a block diagram of a system for regulating the temperature of a plurality of flexible containers for holding biopharmaceutical material, in accordance with the present invention.

In a further embodiment of the present invention, a temperature control unit 1500 may include a plurality of receiving interior portions 1510 for receiving a plurality of flexible containers 1515 adapted to contain biopharmaceutical material, as depicted in FIG. 48. Each receiving interior portion 1510 may include a plurality of heat transfer plates 1520 for regulating a temperature of one of flexible containers 1515. Temperature control unit 1500 is coupled to a temperature regulating unit 1530 for regulating temperatures of plates 1520 wherein temperature regulating unit 1530 is controlled by a controller 1540, programmable by a user. Controller 1540 may also be coupled to one or more temperature sensors (not shown) located in one or more of interior portions 1510 (e.g., on one or more of plates 1520). Feedback from the temperature sensors regarding the temperature of interior portions 1510 may allow controller 1540 to more accurately control the temperature of interior portions 1510 and thus the biopharmaceutical material, when flexible containers 1515 received in interior portions 1510 contain the biopharmaceutical material.

Figure 49:
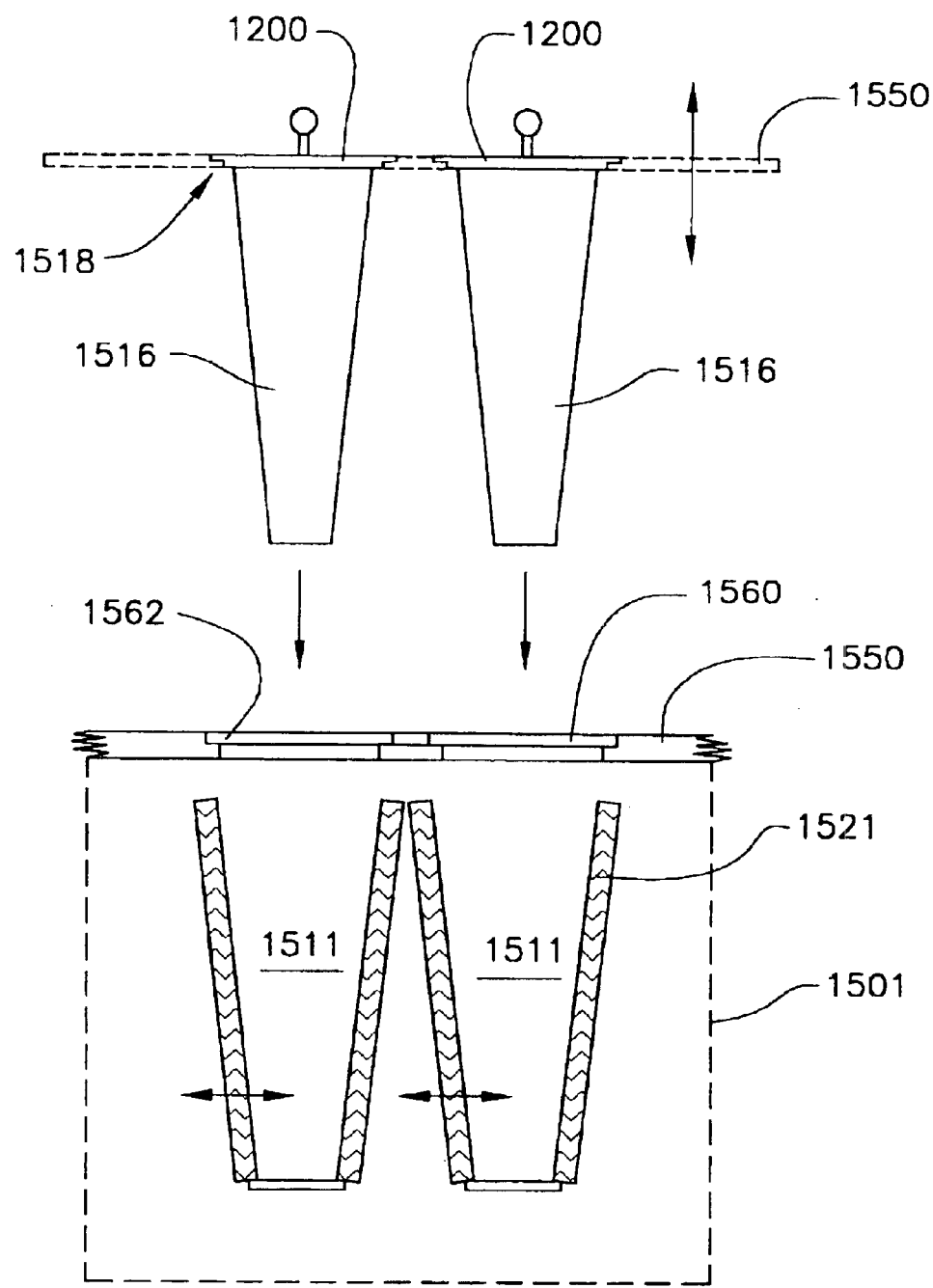
FIG. 49 is a side cross-sectional view of a portion of the system of FIG. 48 having tapered interior portions including a plurality of flexible containers being inserted therein.
Figure 50:
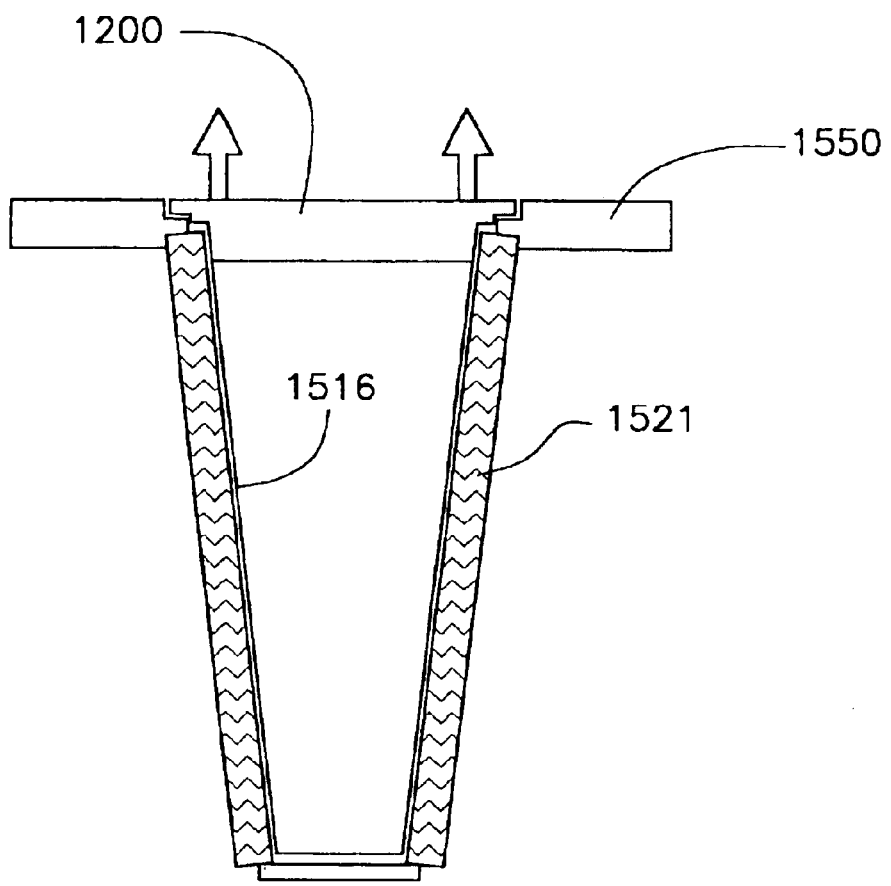
FIG. 50 depicts a side cross-sectional view of the system of FIG. 48 wherein a flexible container is integrally formed with a top plate inserted into a temperature control unit.
Figure 51:
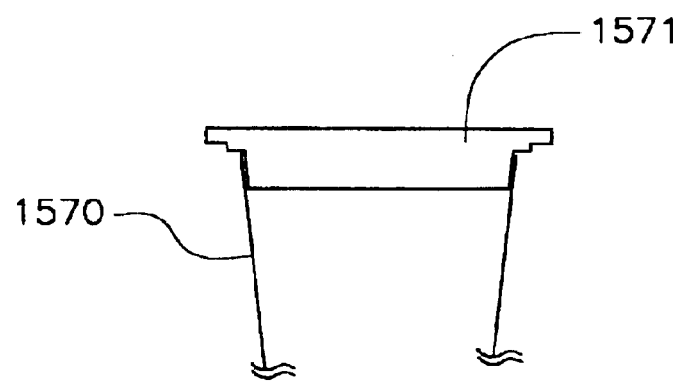
FIG. 51 is a side cross-sectional view of a portion of a flexible container integrally formed with a top plate, in accordance with the present invention.

A temperature control unit 1501, similar to that depicted in FIG. 48, may be adapted to receive or may include a rigid supporting plate 1550 which may be oriented to form a tapered interior 1511, as depicted in FIG. 49. Support plate 1550 may be configured to receive one or more top plates 1200 connected to flexible container 1516. Heat transfer plates 1521 within temperature control unit 1501 may be oriented to form a tapered slot. Support plate 1550 may be formed of polycarbonate, polysulfone or polyethylene via injection-molding or machining, for example, as will be evident to those skilled in the art. Also, top plate 1200 may have notches 1518 adapted to engage receiving notches 1562 of a receiving portion 1560 of rigid supporting plate 1550. Thus, flexible containers 1516 may be inserted into one of interior portions 1511 of temperature control unit 1501 thus engaging top plate 1200 with rigid support plate 1550. Flexible container 1516 may thereby be supported in temperature control unit 1501 for heating or cooling of the biopharmaceutical material therein, as depicted in FIG. 50. It may be possible, as depicted in FIG. 51, to construct a container for holding the biopharmaceutical material as the combination of a flexible container 1570 integrally formed with a rigid or semi-rigid top plate 1571 so that flexible container 1570 and top plate 1571 are formed as a single unit.

Figure 52:
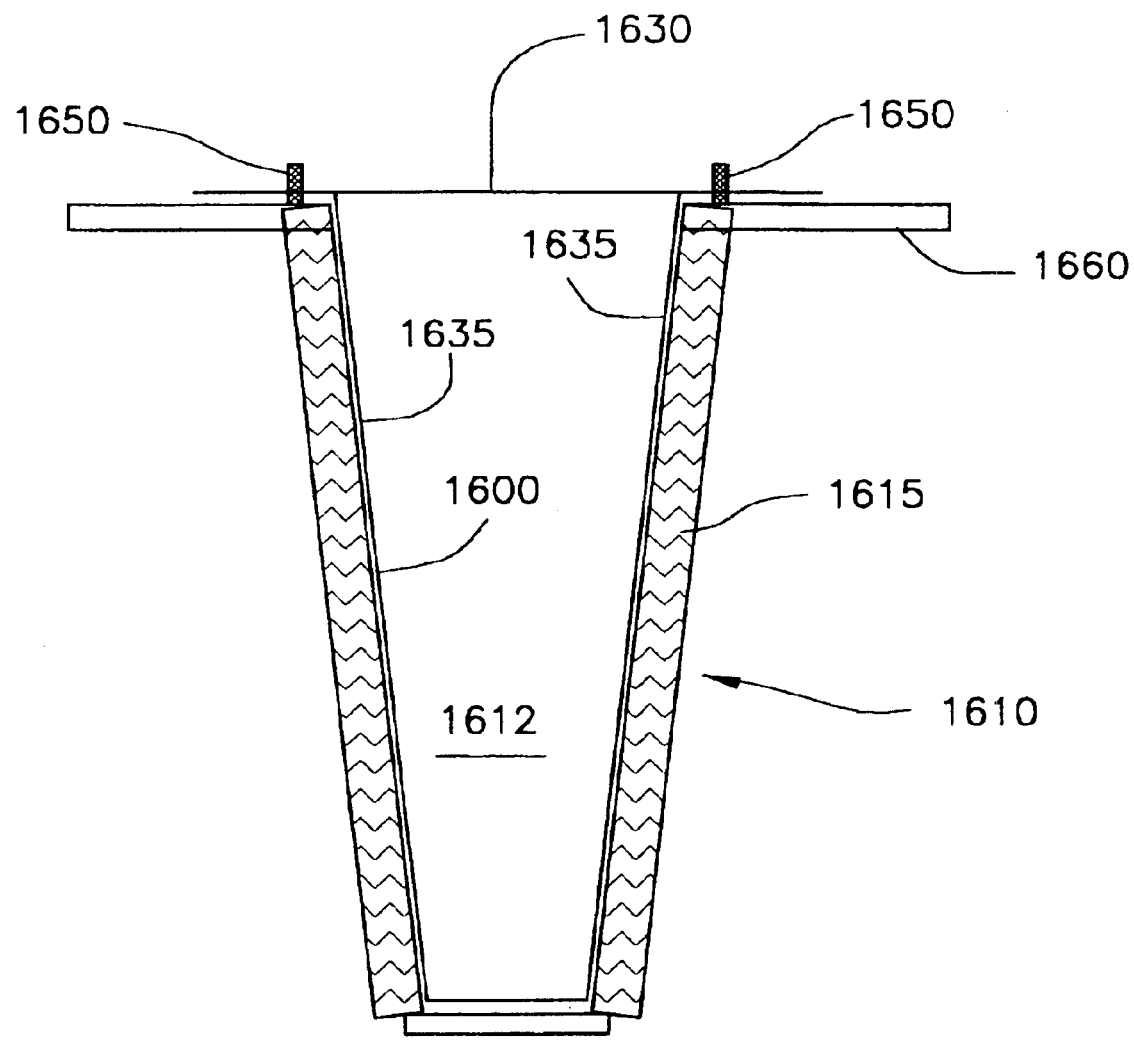
FIG. 52 is a side cross-sectional view of another embodiment of a flexible container for containing biopharmaceutical material being received in a temperature control unit, according to the present invention.
Figure 53:
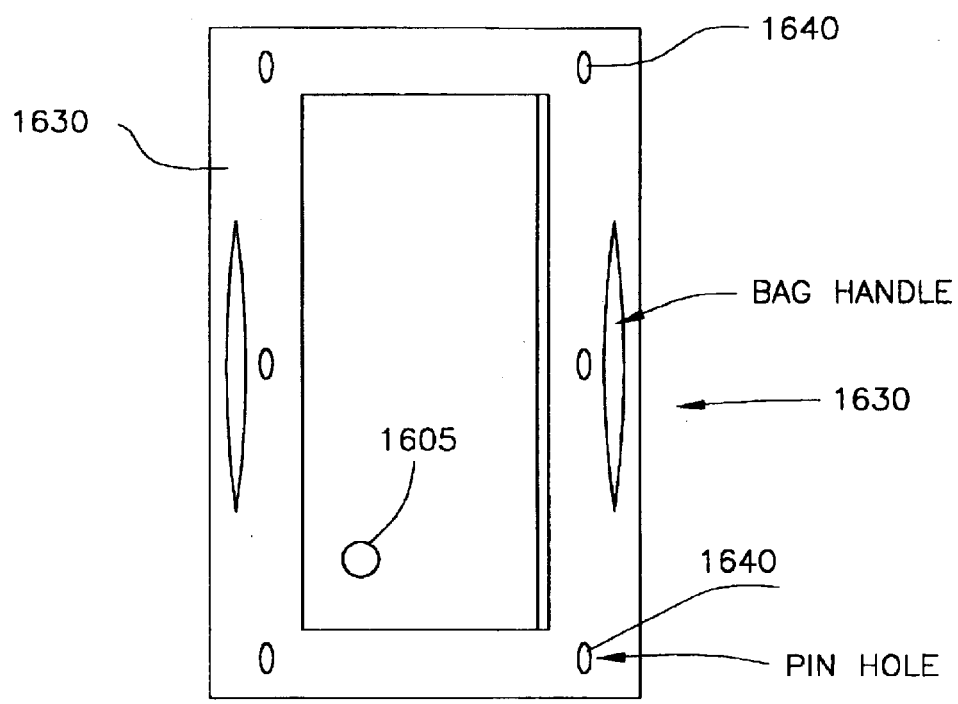
FIG. 53 is a top elevational view of the flexible container and temperature control unit of FIG. 52.
Figure 54:
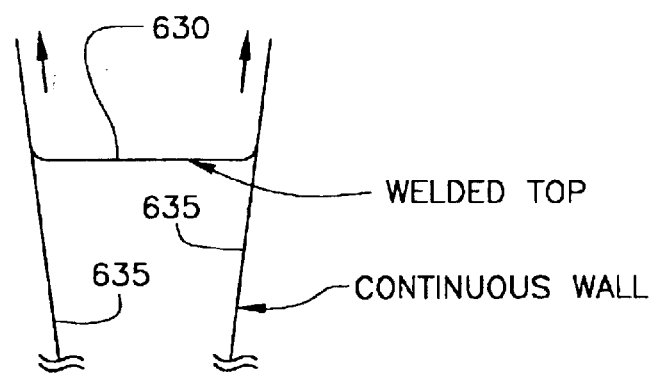
FIG. 54 is a side cross-sectional view of a portion of the flexible container of FIG. 52 further depicting a welding of a top to a continuous wall of the flexible container.

FIGS. 52–54 depict another example of a flexible container 1600 engaged with a cell or an interior portion 1612 of a temperature control unit 1610. Flexible container 1600 includes a flexible top 1630 which includes holes 1640 adapted to receive projections 1650 connected to a top portion 1660 of temperature control unit 1610. Holes 1640 may be aligned with projections 1650 when flexible container 600 is inserted into temperature control unit 1610 to secure flexible container 1600 to top portion 1660. This support of top 1630 of flexible container 1600 is especially useful when flexible container 1600 is being filled via an aperture 1605 in top 1630 of flexible container 1600, because in this instance flexible container 1600 does not yet contain biopharmaceutical material such that side walls or plates 1615 of temperature control unit 1610 may support flexible container 1600 and the contents thereof. Also, a vessel (not shown) for storing flexible container 1600 during transportation or regulated temperature storage thereof may include projections similar to projections 1650 for engaging with holes 1640 to support top 1630 of flexible container 1600. Top portion 1630 may be welded to side walls 1635 of flexible container 1600, as depicted in FIG. 55 as will be understood by those skilled in the art.

Figure 55:
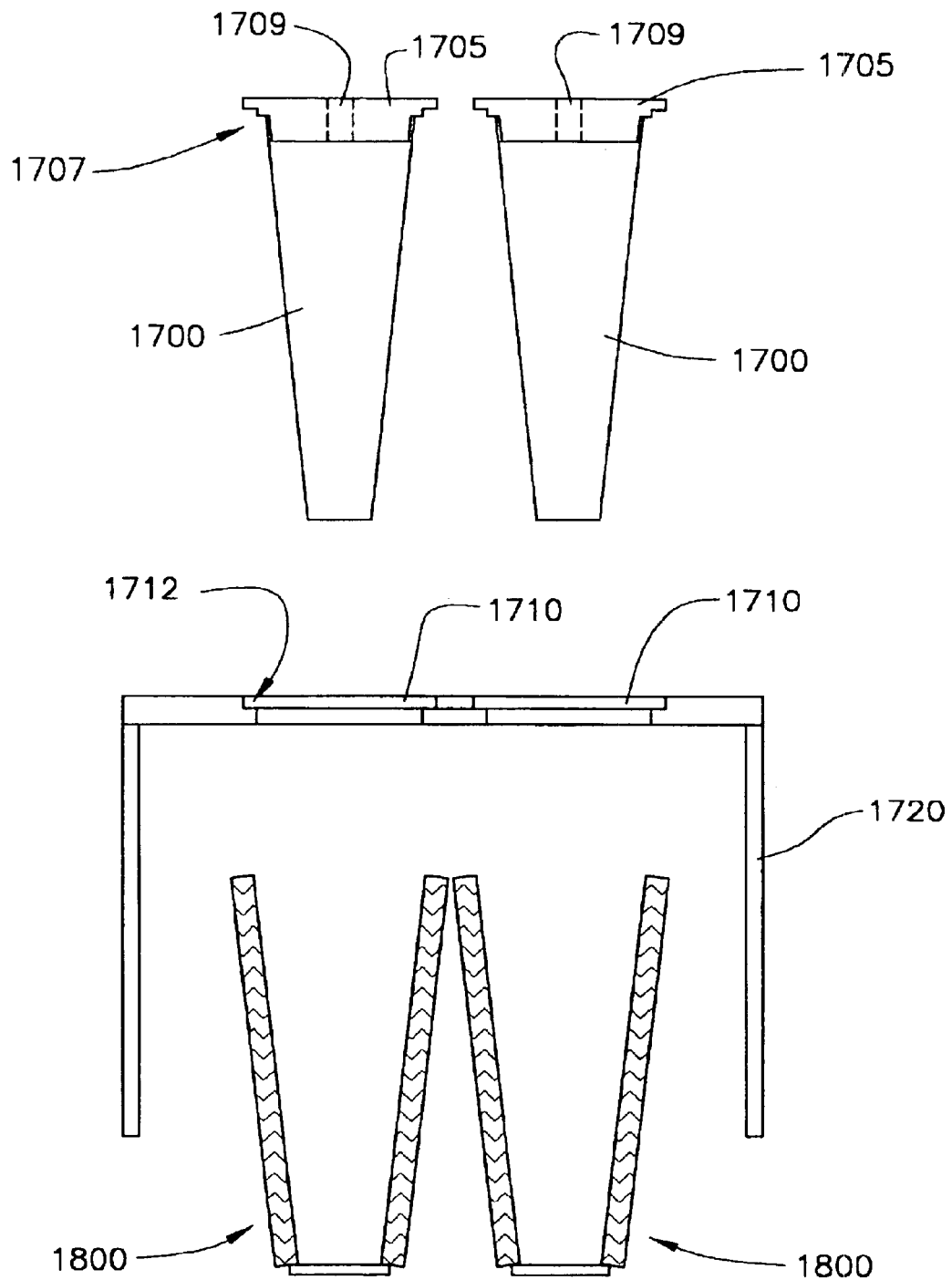
FIG. 55 is a side cross-sectional view of another embodiment of a system for storing biopharmaceutical material, including a plurality of flexible containers receivable in a temperature control unit, in accordance with the present invention.

Another example of a system for freezing, thawing, storage and preservation of a biopharmaceutical material is depicted in FIG. 55. Containers 1700, with biopharmaceutical materials therein with a top plate either integral or removable attached thereto, as previously described, are adapted to engage receiving portions 1710 of a flexible container support structure 1720. Specifically, containers 1700 include top portions 1705 having notches 1707 which may be vertically inserted into notches 1712 of receiving portions 1710 thus supporting containers 1700. Container 1700 may be filled with biopharmaceutical material through apertures 1709 while they are engaged with support structure 1720. When filled, containers 1700 and supporting structure 1720 may be located such that containers 1700 are inserted into temperature control units 1800, as depicted in FIG. 55. The biopharmaceutical material in one or more of containers 1700 may thus be cooled or otherwise regulated in temperature control unit 1800 (e.g., frozen at negative 20 degrees Celsius or below). When such operation is completed, containers 1700 may be removed from temperature control unit 1800 by removing support structure 1720, for example, to a vessel (not shown). The vessel (not shown) or other container large enough to receive support structure 1720, may be stored in a large freezer with an interior air temperature of about negative 20 degrees Celsius, for example.

Another example of a process for freezing, thawing, storing and preserving biopharmaceutical material is described as follows. Flexible container 1010 is inserted into support structure 1032 (FIG. 33) such as vessel 1060 (FIGS. 38–42) and top 1310 is placed thereon, as depicted in FIGS. 41 and 42. Biopharmaceutical material is inserted through opening 1320 and through conduit 1330 into flexible container 1010. Flexible container 1010 is then removed from vessel 1060 and inserted into temperature control unit 1020, as shown in FIG. 33. The biopharmaceutical contents are frozen in temperature control unit 1020 in a controlled manner, for example, such that the freeze rate is controlled within upper and lower limits, as described in U.S. patent application Ser. No. 09/905,488, thus preventing or inhibiting cryoconcentration of the biopharmaceutical material, thereby preventing undesirable degradation of the biopharmaceutical material. After the biopharmaceutical material in flexible container 1010 is frozen, flexible container 1010 may be removed from the temperature control unit 1020 and reinserted into vessel 1060 which may then be placed in a large freezer, for example, a walk-in freezer having an interior air temperature of about negative 20 degrees Celsius, as is typically present in large medical institutions (e.g., hospitals). It will be evident to those skilled in the art from the above description that the contents of flexible container 1516 (FIG. 49) may be frozen or its temperature regulated in temperature control unit 1500 and it may be stored in vessel 1060 (FIGS. 38–42). Further, the contents of flexible container 1600 (FIG. 52) may be frozen in temperature control unit 1610 utilizing plate 1615 and flexible container support holder 1720, and flexible container 1615 may be stored in a vessel adapted to receive flexible container support 1720. It will be further understood by those skilled in the art that modifications may be made to the specific examples described herein and the steps for performing the method for preserving the biopharmaceutical material.

From the above description, it will be understood to one skilled in the art that the flexible containers described herein may be adapted for use in containers, frames, storage units, support structures, transportation devices, temperature control units, heat exchangers, vessels, and/or processors of various shapes or sizes. Further, the frames, containers, support structures, heat exchangers, temperature control unit, vessels, and/or processors may be adapted to receive flexible containers of various shapes or sizes. These frames, vessels, or support structures may be adapted for long or short term storage of the flexible containers containing biopharmaceutical materials in liquid or frozen state, or may be adapted to transport the flexible containers containing biopharmaceutical materials in liquid or frozen state. For example, the storage units, vessels, or transportation devices may be insulated to allow the material to remain at a given temperature for a prolonged period of time. Furthermore, these flexible containers, frames, containers, support structures, temperature control units, heat exchangers, and/or processors may be adapted for utilization with materials other than biopharmaceutical materials. Finally, the storage containers, support structures, vessels, or frames may be equipped with various transport mechanisms, such as wheels, glides, sliders, dry-ice storage compartments or other devices to facilitate transport and organization thereof.

While the invention has been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A container for freezing, storing and thawing a biopharmaceutical material, which is receivable in a support frame, said container comprising:
    a container material having an exterior contact area and an interior configured to receive the biopharmaceutical material therein for freezing, storing and thawing;
    a support structure coupled to said container material, said support structure connectable to the support frame and said support structure configured to support a weight of said container material when said support structure is connected to the support frame and said interior receives the biopharmaceutical material; and
    said support structure being configured to support said container material within the support frame to allow said contact area to be exposed to a contacting surface moveable relative to said frame and to allow a heat transfer surface to contact said container material to allow heat transfer between said heat transfer surface and the biopharmaceutical material.

2. The container of claim 1 wherein said support structure is configured to be received in a channel of the frame configured to receive said support structure.

3. The container of claim 1 wherein said container material forms a container which is compressible within a thickness of the frame.

4. The container of claim 1 further comprising a port to provide fluid communication between an interior of said container material and an exterior of said container material.

5. The container of claim 1 wherein said support structure further comprises an indicator member for receiving display information relating to contents of said container material.

6. The container of claim 1 wherein said support structure further comprises at least one aperture configured to receive at least one post projecting from the frame.

7. The container of claim 1 wherein said support structure further comprises at least one tie-down loop connectable to at least one tie-down boss of the frame.

8. The container of claim 1 wherein said container material comprises at least one of a flexible material and a semi-rigid material.

9. A system for freezing, storing and thawing a biopharmaceutical material, said system comprising:
    a container having an exterior contact area and being configured to receive the biopharmaceutical material therein;
    a frame having a frame interior configured to receive said container, said frame connectable with said container to support said container within said frame interior to allow a moveable contacting surface to contact said contact area to cause a heat transfer surface to contact said contact area to allow heat transfer between said heat transfer surface and the biopharmaceutical material when the biopharmaceutical material is received in said container and said container is received within said frame interior.

10. The system of claim 9 wherein said container comprises a support structure connectable to said frame to support said container within said frame interior.

11. The system of claim 10 wherein said frame further comprises a channel adapted to receive said support structure.

12. The system of claim 10 wherein said support structure comprises at least one aperture, said frame further comprises at least one post projecting from said frame, and wherein said at least one aperture is adapted to receive said at least one post to allow said frame to support said container.

13. The system of claim 12 wherein said frame further comprises a capture member for sandwiching said support structure between said capture member and said frame about said at least one post.

14. The system of claim 12 further comprising a capture member pivotally connected to said frame, wherein said capture member comprises at least one opening to receive said at least one post to connect said capture member, said support structure, and said at least one post.

15. The system of claim 9 further comprising an upright-supporting member connected to said frame, said member configured to hold said frame in an upright position on a surface.

16. The system of claim 10 wherein said frame further comprises an openable top for inhibiting movement of said container out of said frame.

17. The system of claim 9 wherein said frame further comprises a tie-down boss and said container further comprises a tie-down loop, wherein said tie-down boss is engageable with said tie-down loop to connect said frame to said container.

18. The system of claim 17 wherein said tie-down boss is located on an exterior surface of said frame and said frame further comprises an aperture to allow said tie-down loop to pass therethrough to engage said tie-down boss.

19. The system of claim 9 wherein said frame comprises a first portion and a second portion, said first portion being attachable to said second portion to engage said support structure between said first portion and said second portion to connect said container to said frame.

20. The system of claim 9 wherein said frame further comprises at least one opening to allow a temperature of said container to be controlled by the heat transfer surface contacting the contact area, when said container is supported within said frame interior and said frame is received in a temperature control unit.

21. The system of claim 20 further comprising a protective cover for covering at least a portion of said at least one opening to protect said container, when said container is received in said frame.

22. The system of claim 9 wherein said frame comprises a first side having a first opening and a second side having a second opening, wherein said container is in communication with an interior of a temperature control unit through said first opening and said second opening, when said container is received in said frame and said frame is received in said temperature control unit.

23. The system of claim 22 wherein said container comprises a support structure connectable to said frame and configured to allow said container to contact at least one heat transfer surface of said temperature control unit through at least one of said first opening and said second opening of said frame.

24. The system of claim 9 wherein said frame is configured to be received in at least one of a temperature control unit and a storage unit.

25. The system of claim 24 wherein said frame comprises a thickness and a receiving portion of said at least one of a temperature control unit and a storage unit comprises a channel and said thickness is dimensioned to allow said frame to be received in said channel.

26. The system of claim 9 wherein said container comprises an indicator for indicating the contents of said container and said frame comprises a transparent portion to allow said indicator to be analyzed by a user.

27. The system of claim 9 wherein said container is compressible within a thickness of said frame.

28. The system of claim 9 wherein said container comprises at least one of a flexible container and a semi-rigid container.

29. A method for freezing, storing and thawing a biopharmaceutical material, the method comprising:

providing a container having an exterior contact area and an interior configured to contain the biopharmaceutical material for freezing, storing and thawing;

coupling a support structure to the container, the support structure being connectable to a support frame and the support structure being configured to support a weight of the container when the support structure is connected to the support frame and the interior receives the biopharmaceutical material; and configuring the support structure to support the container within the support frame to allow the contact area to be exposed to a contacting surface moveable relative to the frame and to allow a heat transfer surface to contact the container to allow heat transfer between the heat transfer surface and the biopharmaceutical material.

30. The method of claim 29 further comprising the receiving the support structure in a channel of the frame configured to receive the support structure.

31. The method of claim 29 further comprising configuring the container to allow the container to be compressed within a thickness of the frame.

32. The method of claim 29 further comprising connecting a port to the container to provide fluid communication between the interior of the container and an exterior of the container.

33. The method of claim 29 further comprising connecting an indicator member to the support structure, the indicator member being configured to receive display information relating to contents of the container.

34. The method of claim 29 wherein the support structure comprises at least one aperture configured to receive at least one post projecting from the frame.

35. The method of claim 29 wherein the support structure comprises at least one tie-down loop connectable to at least one tie-down post of the frame.

36. The method of claim 29 further comprising forming the container of at least one of a flexible material and a semi-rigid material.

* * * * *